United States Patent
Ginn et al.

(10) Patent No.: US 6,695,867 B2
(45) Date of Patent: Feb. 24, 2004

(54) PLUNGER APPARATUS AND METHODS FOR DELIVERING A CLOSURE DEVICE

(75) Inventors: Richard S. Ginn, San Jose, CA (US); Anthony Pantages, Los Altos, CA (US)

(73) Assignee: Integrated Vascular Systems, Inc., Sunnyvale, CA (US)

( * ) Notice: Subject to any disclaimer, the term of this patent is extended or adjusted under 35 U.S.C. 154(b) by 117 days.

(21) Appl. No.: 10/081,717

(22) Filed: Feb. 21, 2002

(65) Prior Publication Data

US 2003/0158577 A1 Aug. 21, 2003

(51) Int. Cl.[7] .............................................. A61B 17/08
(52) U.S. Cl. ...................................... 606/213; 606/142
(58) Field of Search ............................... 606/139, 140, 606/141, 142, 143, 144, 151, 152, 153, 154, 155, 156, 157, 158, 213, 215, 216, 219, 220, 185, 186, 75, 221, 104; 227/179.1, 175.1

(56) References Cited

U.S. PATENT DOCUMENTS

| | | |
|---|---|---|
| 3,586,002 A | 6/1971 | Wood |
| 3,604,425 A | 9/1971 | LeRoy |
| 3,677,243 A | 7/1972 | Nerz |
| 3,757,629 A | 9/1973 | Schneider |
| 3,805,337 A | 4/1974 | Branstetter |
| 4,192,315 A | 3/1980 | Hilzinger et al. |
| 4,217,902 A | 8/1980 | March |
| 4,345,606 A | 8/1982 | Littleford |
| 4,396,139 A | 8/1983 | Hall et al. |
| 4,411,654 A | 10/1983 | Boarini et al. |
| 4,412,832 A | 11/1983 | Kling et al. |
| 4,485,816 A | 12/1984 | Krumme |
| RE31,855 E | 3/1985 | Osborn |
| 4,505,274 A | 3/1985 | Speelman |
| 4,586,503 A | 5/1986 | Kirsch et al. |
| 4,687,469 A | 8/1987 | Osypka |
| 4,772,266 A | 9/1988 | Groshong |

(List continued on next page.)

OTHER PUBLICATIONS

PCT Publication No. WO 00/07640, "Vascular Suction Cannula, Dialator and Surgical Stapler", Feb. 17, 2000.
PCT Publication No. WO 00/56227, entitled "Advanced Closure Device", Sep. 28, 2000.
PCT Publication No. WO 00/56227, entitled "Advanced Closure Device", Sep. 28, 2000.
PCT Publication No. WO 00/56223, entitled "Vascular Closure Device", Sep. 28, 2000.

*Primary Examiner*—Michael J. Milano
*Assistant Examiner*—D. Jacob Davis
(74) *Attorney, Agent, or Firm*—Orrick, Herrington & Sutcliffe LLP; James W. Geriak

(57) ABSTRACT

An apparatus for delivering a clip includes an introducer sheath including an outer surface extending between its proximal and distal ends, and a hub on the proximal end that includes spacer elements spaced away from the outer surface. An annular clip includes a plurality of tines extending from its distal end and its proximal end is held away from the outer surface of the sheath by the spacer elements. A handle assembly is attached to the hub that includes an actuator member slidable between the spacer elements and the outer surface of the sheath. The actuator member includes radial protrusions for coupling with the clip, whereby distal movement of the actuator member advances the clip towards the distal end of the sheath. Optionally, a skin overlies the outer surface of the sheath and the clip that is separable from the outer surface as the clip is advanced.

38 Claims, 8 Drawing Sheets

U.S. PATENT DOCUMENTS

| | | |
|---|---|---|
| 4,777,950 A | 10/1988 | Kees, Jr. |
| 4,860,746 A | 8/1989 | Yoon |
| 4,865,026 A | 9/1989 | Barrett |
| 4,917,087 A | 4/1990 | Walsh et al. |
| 4,950,258 A | 8/1990 | Kawai et al. |
| 5,007,921 A | 4/1991 | Brown |
| 5,026,390 A | 6/1991 | Brown |
| 5,053,008 A | 10/1991 | Bajaj |
| 5,108,420 A | 4/1992 | Marks |
| 5,156,609 A | 10/1992 | Nakao et al. |
| 5,167,634 A | 12/1992 | Corrigan |
| 5,176,648 A | 1/1993 | Holmes et al. |
| 5,192,302 A | 3/1993 | Kensey et al. |
| 5,222,974 A | 6/1993 | Kensey et al. |
| 5,275,616 A | 1/1994 | Fowler |
| 5,304,184 A | 4/1994 | Hathaway et al. |
| 5,318,542 A | 6/1994 | Hirsch et al. |
| 5,334,217 A | 8/1994 | Das |
| 5,366,458 A | 11/1994 | Korthoff et al. |
| 5,478,354 A | 12/1995 | Tovey et al. |
| 5,527,322 A | 6/1996 | Klein et al. |
| 5,674,231 A | 10/1997 | Green et al. |
| 5,683,405 A | 11/1997 | Yacoubian et al. |
| 5,695,505 A | 12/1997 | Yoon |
| 5,782,844 A | 7/1998 | Yoon et al. |
| 5,782,860 A | 7/1998 | Epstein et al. |
| 5,782,861 A | 7/1998 | Cragg et al. |
| 5,810,846 A | 9/1998 | Virnich et al. |
| 5,810,851 A | 9/1998 | Yoon |
| 5,817,113 A | 10/1998 | Gifford |
| 5,820,631 A | 10/1998 | Nobles |
| 5,830,125 A | 11/1998 | Scribner et al. |
| 5,879,366 A | 3/1999 | Shaw et al. |
| 5,910,155 A | 6/1999 | Ratcliff et al. |
| 5,922,009 A | 7/1999 | Epstein et al. |
| 5,951,518 A | 9/1999 | Licata et al. |
| 5,951,589 A | 9/1999 | Epstein et al. |
| 5,964,782 A | 10/1999 | LaFontaine et al. |
| 5,984,934 A | 11/1999 | Ashby et al. |
| 5,993,468 A * | 11/1999 | Rygaard ............... 606/151 |
| 6,007,563 A | 12/1999 | Nash et al. |
| 6,036,720 A | 3/2000 | Abrams et al. |
| 6,045,570 A | 4/2000 | Epstein et al. |
| 6,056,769 A | 5/2000 | Epstein et al. |
| 6,056,770 A | 5/2000 | Epstein et al. |
| 6,063,085 A | 5/2000 | Tay et al. |
| 6,077,281 A | 6/2000 | Das |
| 6,077,291 A | 6/2000 | Das |
| 6,080,182 A | 6/2000 | Shaw |
| 6,080,183 A | 6/2000 | Tsugita et al. |
| 6,113,612 A | 9/2000 | Swanson et al. |
| 6,120,524 A | 9/2000 | Taheri |
| 6,152,937 A | 11/2000 | Peterson et al. |
| 6,197,042 B1 * | 3/2001 | Ginn et al. ............ 606/213 |
| 6,348,064 B1 | 2/2002 | Kanner |
| 6,391,048 B1 * | 5/2002 | Ginn et al. ............ 606/213 |
| 6,461,364 B1 * | 10/2002 | Ginn et al. ............ 606/142 |
| 2001/0031972 A1 * | 10/2001 | Robertson et al. ........ 606/139 |
| 2003/0009180 A1 | 1/2003 | Hinchliffe et al. |
| 2003/0093096 A1 | 5/2003 | McGuckin et al. |

* cited by examiner

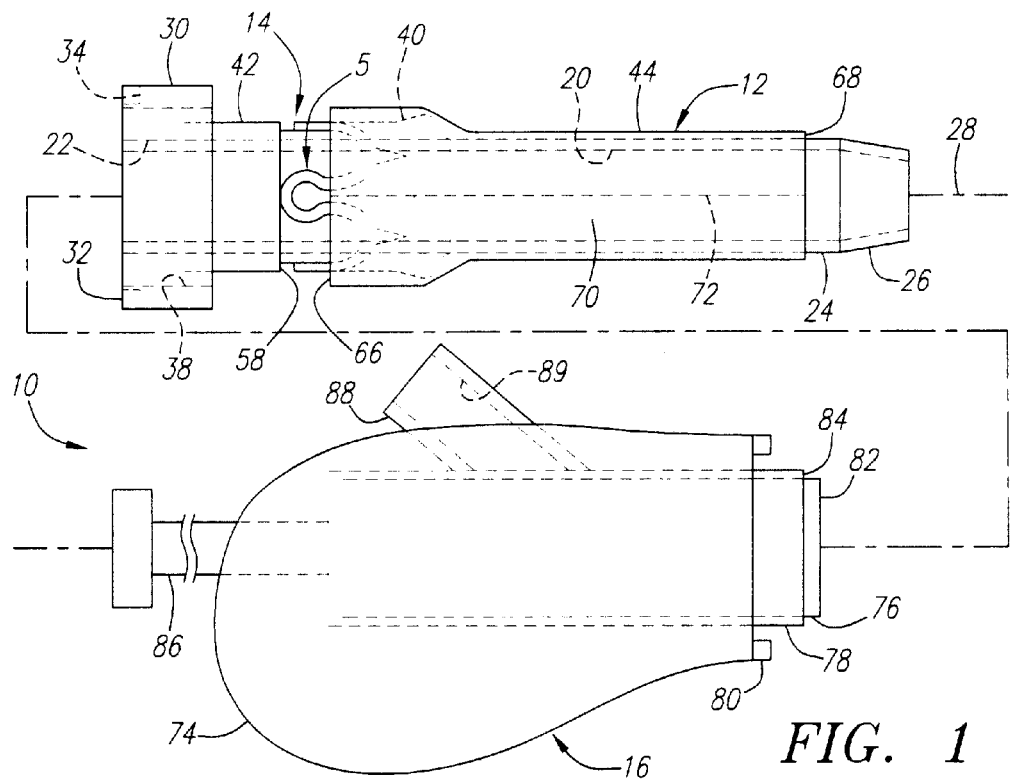
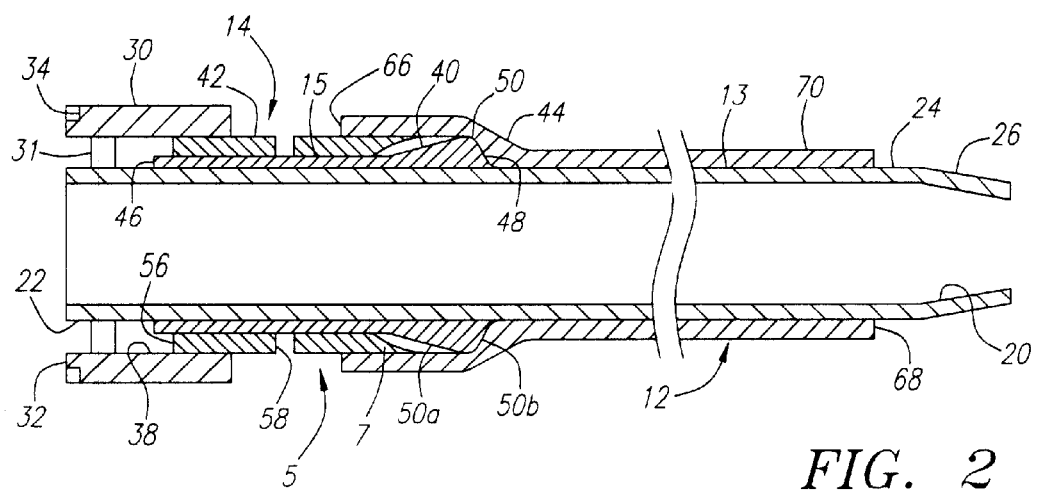
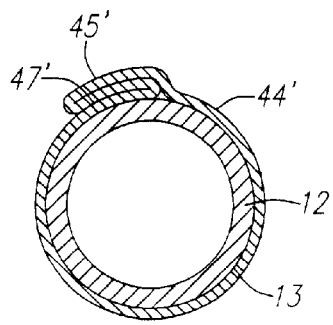
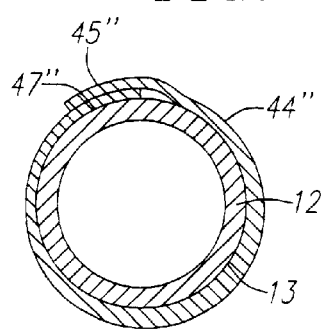
FIG. 1
FIG. 2
FIG. 3A
FIG. 3B

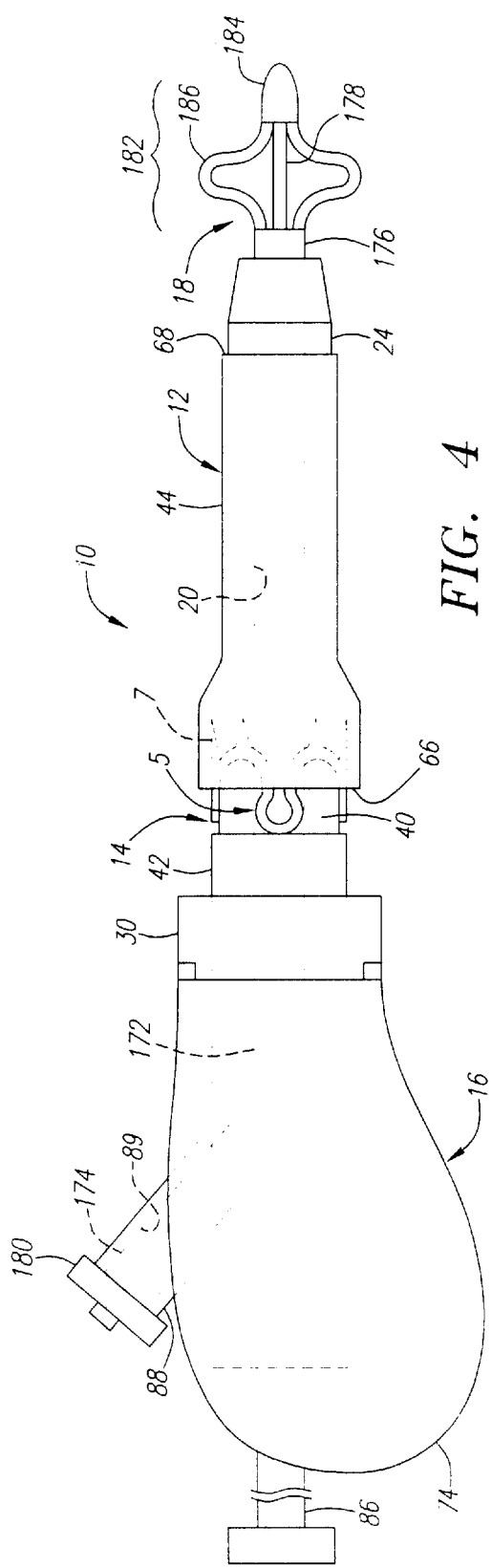
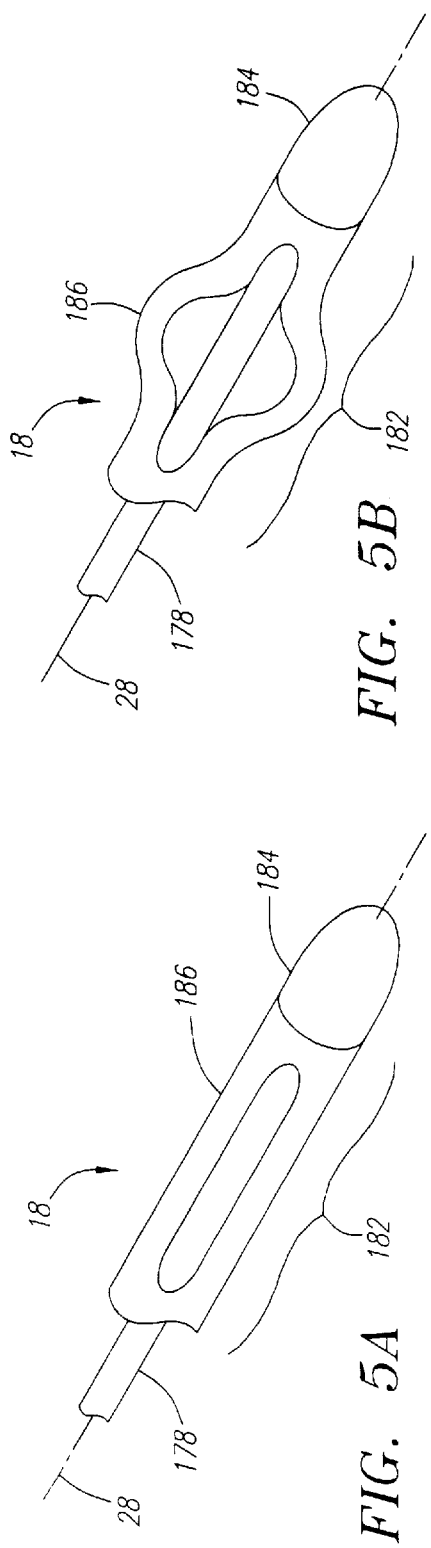
FIG. 4
FIG. 5A
FIG. 5B

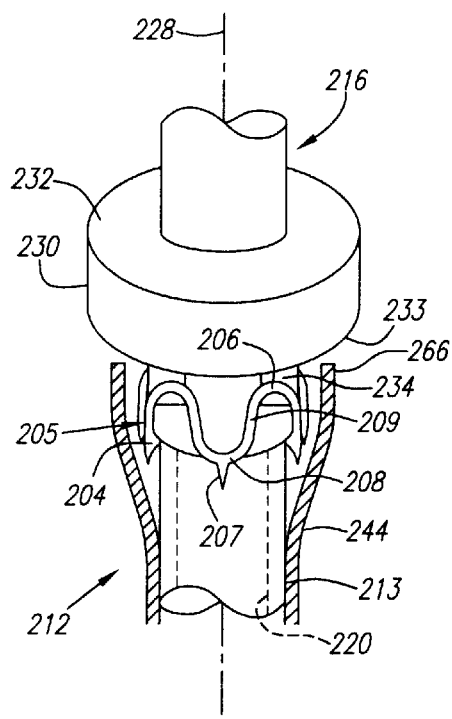
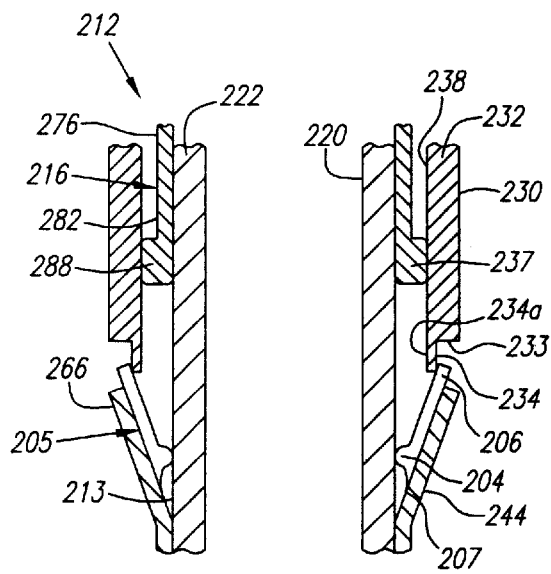
FIG. 8
FIG. 9A
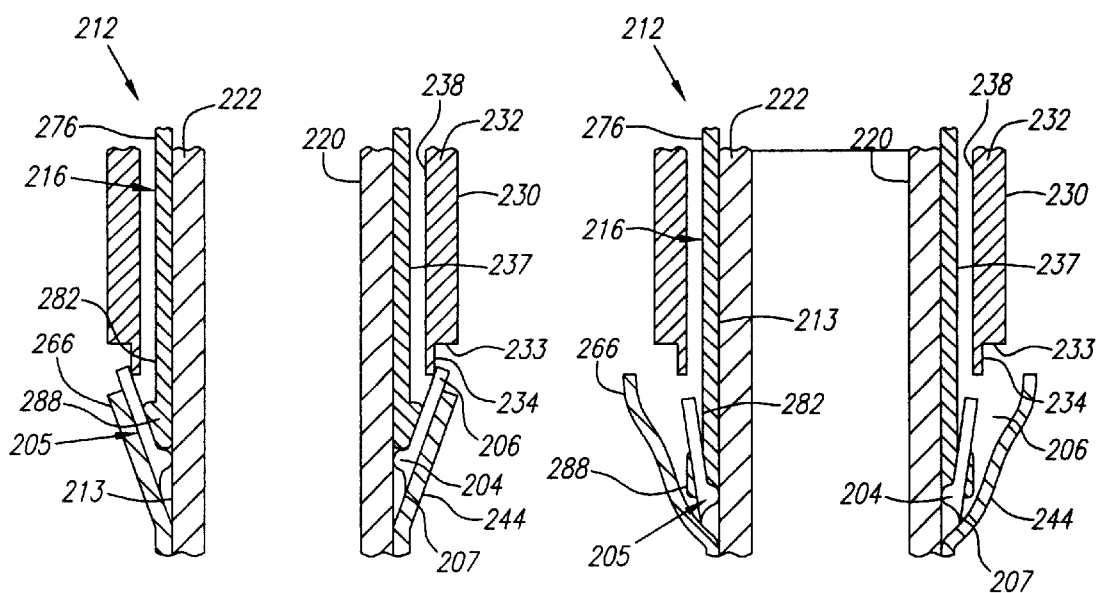
FIG. 9B
FIG. 9C

PLUNGER APPARATUS AND METHODS FOR DELIVERING A CLOSURE DEVICE

FIELD OF THE INVENTION

The present invention relates generally to apparatus and methods for closing and/or sealing openings through tissue, and more particularly to apparatus and methods for delivering a closure element for closing a puncture in a blood vessel or other body lumen formed during a diagnostic or therapeutic procedure.

BACKGROUND

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

To facilitate positioning devices that are percutaneously inserted into a blood vessel, "bleed back" indicators have been suggested. For example, U.S. Pat. No. 5,676,974, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel. The loop may also provide a support for facilitating the deployment and deflection of a surgical clip against the vessel wall. Such a device, however, may risk engagement between the loop and the surgical clip, thereby preventing the loop from being withdrawn from the vessel.

Accordingly, apparatus and methods for delivering a device for closing a vascular puncture site or other opening through tissue would be useful.

SUMMARY OF THE INVENTION

The present invention is directed to apparatus and methods for closing and/or sealing openings through tissue, e.g., into body lumens, and more particularly to apparatus and methods for delivering a vascular closure element for closing a puncture in a blood vessel formed during a diagnostic or therapeutic procedure.

In accordance with one aspect of the present invention, an apparatus is provided for delivering a closure element or other annular-shaped device into an opening through tissue, e.g., for engaging tissue adjacent the opening to close and/or seal the opening. The apparatus generally includes an elongate member including proximal and distal ends defining a longitudinal axis therebetween, and an outer surface extending between the proximal and distal ends. In one embodiment, the elongate member may be an introducer sheath that includes a lumen for advancing one or more devices into a body lumen during a procedure.

A carrier assembly may be slidable on the elongate member from the proximal end towards the distal end, the carrier assembly including a carrier member and a pusher member movable distally relative to the carrier member. A distal end of the pusher member may be disposed proximal to a distal end of the carrier member, e.g., if the pusher member has a substantially shorter length than the carrier member, thereby defining a space distal to the pusher member along an outer surface of the carrier member. An annular-shaped element, e.g., a clip or other closure device, may be received on the carrier member, the annular-shaped element being deployable from the carrier member upon distal movement of the pusher member relative to the carrier member.

Optionally, the carrier member may include one or more ramped portions, each portion defining a ramped distal surface and/or a ramped proximal surface. The closure element may include a plurality of tines extending distally, the tines being disposed proximal to the one or more ramped portions such that the ramped portions may protect the tines during advancement of the carrier assembly. In addition, the pusher member may advance the closure element over the one or more ramped portions when the carrier assembly is advanced to a distal position, e.g., for directing the tines radially outwardly to engage surrounding tissue.

A skin overlies at least a portion of the outer surface of the elongate member and the carrier assembly, the skin being separable from the outer surface of the elongate member as the carrier assembly is advanced from the proximal end towards the distal end of the elongate member. In one embodiment, the skin may include a weakened region, e.g., a thin and/or perforated region, extending axially along the skin. The weakened region may be configured to tear preferentially as the carrier assembly is advanced from the proximal end towards the distal end of the elongate member.

In another embodiment, the skin may include a flap extending axially along the outer surface of the elongate member and overlying an adjacent region of the skin. The flap may be bonded to the adjacent region such that the flap may be separated from the adjacent region as the carrier assembly is advanced towards the distal end of the elongate member.

In addition or alternatively, the skin may be bonded to the outer surface of the elongate member by an adhesive. The adhesive may have sufficient adhesive strength such that the skin may be peeled away from the outer surface as the carrier assembly is advanced towards the distal end of the elongate member.

The apparatus may also include an actuator assembly including a housing extending from the proximal end of the elongate member, e.g., connectable by cooperating detents, and one or more elongate actuator elements that are movable axially relative to the housing. The actuator elements may be connected to the carrier assembly for coupling movement of the carrier assembly to the one or more actuator elements. For example, the carrier assembly and the actuator elements may include cooperating detents for coupling distal movement of the carrier assembly to the one or more actuator elements as the control member is directed distally. The cooperating detents may release the carrier member upon attaining a distal position, thereby permitting further distal movement of the pusher member to deploy the closure element from the carrier member.

During use, the distal end of the elongate member may be inserted into an opening through tissue, e.g., into a puncture communicating with an artery or other blood vessel. If the elongate member is an introducer sheath, one or more instruments may be inserted through the sheath, e.g., into a blood vessel accessed via the opening. A diagnostic and/or therapeutic procedure may be performed within a patient's body, e.g., via the blood vessel accessed via the opening. Upon completion of the procedure, any instruments may be removed from the sheath, the handle assembly may be connected to the proximal end of the elongate member, and/or an actuator may be coupled to the carrier assembly. Optionally, the distal end of the elongate member may be positioned relative to the blood vessel, e.g., using a bleed-back indicator or a tactile indicator, such as an expandable obturator.

To deploy the closure element, the carrier assembly may be advanced towards the distal end of the elongate member. The carrier assembly may cause the skin to separate from the outer surface of the elongate member as the carrier assembly is advanced towards the distal end. If the skin includes a weakened region extending towards the distal end of the elongate member, the weakened region may tear preferentially as the carrier assembly is advanced towards the distal end of the elongate member. If the skin includes a flap extending axially along the outer surface of the elongate member and overlying an adjacent region of the skin, the flap may be released from the adjacent region as the carrier assembly is advanced towards the distal end of the elongate member, thereby allowing the skin to separate from the outer surface. In addition or alternatively, if the skin is bonded to the outer surface of the elongate member by an adhesive, the adhesive may have sufficient adhesive strength to release as the carrier assembly directs the skin outwardly such that the skin is separated from the outer surface as the carrier assembly is advanced towards the distal end.

As the carrier assembly is advanced, the carrier assembly may pass between the skin and the outer surface of the elongate member. Thus, if the opening through tissue extends through one or more layers of fascia or other tissue structures, the skin may facilitate advancing the carrier assembly through the layers and/or minimize the risk of the carrier assembly or the closure element catching on tissue as it is advanced towards the distal end of the elongate member.

The closure element may be deployed from the carrier assembly within the opening, e.g., by ejecting the closure element from the carrier assembly and/or by withdrawing the elongate member from the opening. With the elongate member withdrawn, the closure element may substantially close or seal the opening, e.g., to prevent blood flow therethrough, thereby allowing the opening to heal.

In accordance with another aspect of the present invention, an apparatus is provided for delivering a closure device that includes an elongate member, e.g., an introducer sheath, including proximal and distal ends defining a longitudinal axis therebetween, and an outer surface extending between the proximal and distal ends. A hub may be provided on the proximal end of the elongate member, the hub including one or more alignment tabs or spacers disposed about the periphery of the hub and/or spaced away from the outer surface of the elongate member.

A closure element, e.g., a clip, may be provided that includes a generally annular-shaped body including proximal and distal ends and a plurality of tissue engaging portions extending from the distal end. The proximal end of the closure element may be held away from the outer surface of the elongate member by the one or more spacers.

An actuator or handle assembly is provided that includes an actuator member slidable between the hub and the outer surface of the elongate member. The actuator member includes one or more elements for coupling with the closure element, whereby distal movement of the actuator member advances the closure element towards the distal end of the elongate member. In one embodiment, the hub may include an annular hub defining a passage between the annular hub and the outer surface of the elongate member, e.g., attached to the elongate member by one or more radial spokes. The actuator member may include a tubular member, e.g., defining a "C" shaped cross-section for inserting the tubular member through the passage around the one or more radial spokes.

In a preferred embodiment, the tubular member may include one or more protrusions or tabs, e.g., extending radially outwardly from the distal end of the tubular member. The closure element may include a plurality of pockets for receiving respective tabs on the tubular member therein, thereby coupling the closure element to the tubular member using the tabs. For example, the closure element may include a plurality of alternating diagonal elements extending between the proximal and distal ends of the closure element. The distal end of the closure element may include curved elements connecting adjacent diagonal elements, the curved elements defining the pockets.

Optionally, a skin may overlie at least a portion of the outer surface of the elongate member between the carrier assembly and the distal end of the elongate member, and may at least partially overlie the closure element. The skin may be separable from the outer surface as the closure element is advanced towards the distal end of the elongate member, similar to the previous embodiment.

During use, the distal end of the elongate member may be inserted into an opening through tissue, e.g., into a puncture communicating with a blood vessel, and a procedure may be performed, similar to the previous embodiment. Upon completing the procedure, a distal end of the actuator member may be inserted between the hub and the outer surface of the elongate member. Thus, the actuator member may pass under the spacers, and consequently, under the proximal end of the closure element, until the distal end of the actuator member is coupled with the closure element, e.g., received in pockets adjacent the distal end of the closure element. The actuator member may be advanced distally, thereby advancing the closure element towards the distal end of the elongate member. Tissue adjacent the distal end of the elongate member may be engaged with tissue engaging elements on the closure element, and the elongate member may be withdrawn from the opening, leaving the closure element to close and/or seal the opening. Alternatively, the closure element may be carried by the distal end of the actuator member, rather than being disposed initially adjacent the hub. In this alternative, the closure element may be introduced between the hub and the elongate member when the actuator member is connected to the hub, and advanced along the elongate member as the actuator member is advanced.

Other objects and features of the present invention will become apparent from consideration of the following description taken in conjunction with the accompanying drawings.

BRIEF DESCRIPTION OF THE DRAWINGS

FIG. 1 is an exploded side view of a first preferred embodiment of an apparatus for delivering a closure element, including an introducer sheath, an actuator assembly, and an obturator, in accordance with the present invention.

FIG. 2 is a cross-sectional side view of the apparatus of FIG. 1.

FIGS. 3A and 3B are cross-sectional views of alternative embodiments of the introducer sheath of FIG. 1.

FIG. 4 is a side view of the apparatus of FIG. 1, with the actuator assembly connected to the sheath, and an obturator inserted through the actuator assembly and sheath.

FIGS. 5A and 5B are perspective views of the distal end of the obturator of FIG. 4, showing positioning elements on the obturator in collapsed and expanded configurations, respectively.

FIG. 8 is a perspective detail of the apparatus of FIG. 7 with the actuator assembly attached to the introducer sheath.

FIGS. 9A–9C are cross-sectional details of the apparatus of FIGS. 7 and 8.

DETAILED DESCRIPTION OF THE PREFERRED EMBODIMENTS

Figure 6A:
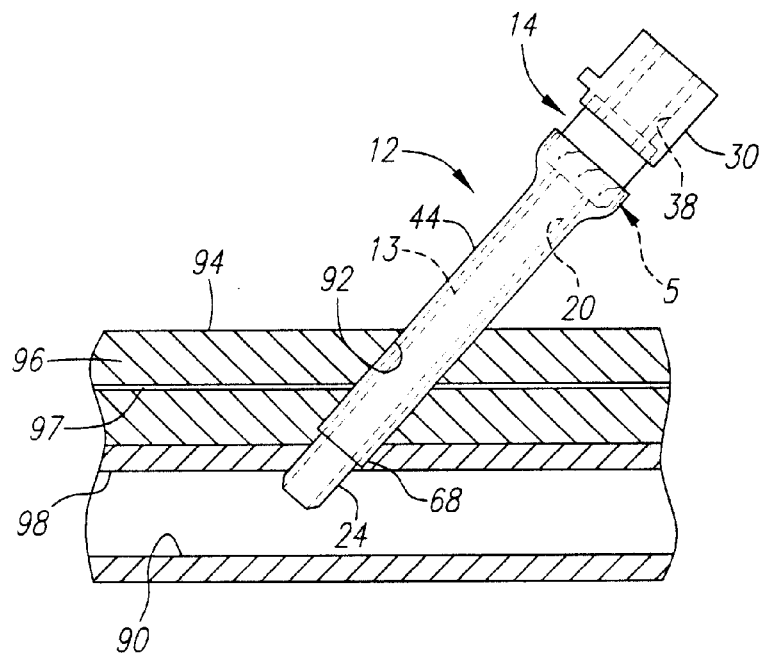
FIGS. 6A–6G are cross-sectional views of a blood vessel, showing a method for delivering a clip into with a wall of the vessel.

Turning now to the drawings, FIGS. 1, 2, and 4 show a first preferred embodiment of an apparatus 10 for delivering a closure element, such as a clip 5, into an opening through tissue for closing and/or sealing the opening (not shown). Generally, the apparatus 10 includes an introducer sheath 12, a housing or carrier assembly 14 slidably disposed on the sheath 12, and a skin 44 overlying the sheath 12 and/or carrier assembly 14. The apparatus 10 may also include an actuator or handle assembly 16 that is connectable to the sheath 12. Optionally, as shown in FIG. 4, the apparatus 10 may also include a locator member or obturator 18 that may be insertable through the actuator assembly 16 and/or sheath 12 for assisting positioning of the apparatus, as described further below.

The sheath 12 is generally a substantially flexible or semi-rigid tubular member including a lumen 20 extending along a longitudinal axis 28 between its proximal and distal ends 22, 24. The distal end 24 has a size and shape to facilitate insertion into an opening through tissue (not shown), e.g., having a tapered tip 26 for facilitating substantially atraumatic introduction through a passage and/or at least partially into a blood vessel or other body lumen accessed via the passage. The lumen 20 has a size for accommodating insertion of one or more devices therethrough, such as a catheter, guidewire, and the like (not shown). The sheath 12 may also include a seal (not shown), such as a hemostatic valve, within the lumen 20, e.g., at or near the proximal end 22, that may provide a fluid-tight seal, yet accommodate inserting one or more devices, such as the obturator 18, into the lumen 20 without fluid passing proximally from the sheath 12.

An annular hub 30 may be provided on the proximal end 22 of the sheath 12, e.g., attached by one or more radial spokes, such as the spoke 31 shown in FIG. 2. Preferably, the hub 30 and the sheath 12 define a "C" shaped passage 38 (or multiple passages if multiple spokes are provided) therebetween that extends substantially parallel to the longitudinal axis 28. In addition, the hub 30 may include one or more connectors on its proximal end 32, such as recesses or pockets 34, for cooperating with mating connectors 80 on the actuator assembly 16, as described further below. Alternatively, the actuator assembly 16 may be connectable directly to the proximal end 22 of the sheath 12 (not shown), may be provided as an integral component of the sheath 12 (not shown), or may otherwise extend from the proximal end 22 of the sheath 12, e.g., such that the hub 30 may be eliminated.

Optionally, the hub 30 may include a side port (not shown) that communicates with the lumen 20, for example, to allow infusion of fluids into the lumen 20 through the sheath 12. Alternatively, or in addition, the side port may be used to provide a "bleed back" indicator, such as that disclosed in co-pending application Ser. No. 09/680,837, filed Oct. 6, 2000, which is assigned to the assignee of the present invention. The disclosure of this application and any references cited therein are expressly incorporated herein by reference.

In a further alternative, the spokes 31 may be eliminated from the hub 30, and the hub 30 may be secured to the sheath 12 by an annular seal or other frictional member (not shown). When the actuator assembly 16 is attached to the sheath 12, as described further below, the hub 30 may at least partially break away or may be secured to the actuator assembly 16. The actuator assembly 16 and/or the obturator 18 may frictionally or mechanically become secured to the sheath 12 to prevent the apparatus 10 from separating during use.

The carrier assembly 14 is slidably disposed on an outer surface 13 of the sheath 12 and is configured for releasably holding the clip 5. The carrier assembly 14 is slidable from a proximal position, e.g., adjacent the hub 30, and preferably at least partially disposed within the passage 38, towards the distal end 24 of the sheath 12.

With particular reference to FIG. 2, the carrier assembly 14 may include an inner or carrier member 40 and an outer or pusher member 42 that are nested together and coaxially disposed around the sheath 12. The carrier member 40 is an annular-shaped body including proximal and distal ends 46, 48, and a ramped region 50 adjacent the distal end 48. The ramped region 50 may include a ramped proximal surface 50a, e.g., for facilitating deployment of the clip 5 over the ramped region 50, and/or a ramped distal surface 50b, e.g., for facilitating advancement of the carrier assembly 14, as described further below. The distal end 48 of the carrier member 40 may be tapered, and/or, alternatively, the carrier member 40 may include a plurality of ramped regions (not shown) adjacent the distal end 48, rather than a single annular ramped region, e.g., spaced evenly about a perimeter or other periphery of the carrier member 40.

The carrier member 40 may include a connector (not shown) on the proximal end 46 for coupling the carrier member 40 to the actuator assembly 16. Alternatively, the carrier member 40 may be coupled to the hub 30 and/or to the proximal end 22 of the sheath 12 by a tether or other element (not shown) for limiting distal movement of the carrier member 40, as described further below.

The pusher member 42 may also be an annular body, including proximal and distal ends 56, 58 and may include a connector (not shown) on its proximal end 56 for coupling the pusher member 42 to the actuator assembly 16. The distal end 58 may be substantially blunt to engage the clip 5, e.g., to advance or deploy the clip 5 from the carrier assembly 14, as described further below. The pusher member 42 is configured to slidably fit around the carrier member 40, but has a substantially shorter length than the carrier member 40, such that the carrier and pusher members 40, 42 define a space 15 distal to the distal end 58 of the pusher member 42 and along an outer surface of the carrier member 40 for receiving the clip 5.

The carrier assembly 14 may be used to deploy a clip 5 or other closure element from the space 15 defined by the carrier assembly 14. In a preferred embodiment, the clip 5 is a generally annular-shaped body, including one or more tines 7 for engaging the tissue around an opening, e.g., adjacent to a wall of a blood vessel (not shown). Preferably, the clip 5 is configured for drawing the tissue around a puncture in the wall of a blood vessel substantially closed and/or sealed, e.g., for enhancing hemostasis within the puncture. Exemplary embodiments of a closure element for use with an apparatus in accordance with the present invention are disclosed in U.S. Pat. No. 6,197,042, and in co-pending application Ser. Nos. 09/546,998 and 09/610,238, the disclosures of which are expressly incorporated herein by reference.

The carrier assembly 14 may be actuated from the proximal end 22 of the sheath 12, preferably by the actuator assembly 16, as explained further below. The carrier assembly 14 may be substantially permanently but slidably disposed on the sheath 12. For example, the carrier assembly 14 may be initially stored at least partially within the passage 38 under the hub 30. Alternatively, the carrier assembly 14 may be provided separate from the sheath 12 (not shown), e.g., with the clip 5 pre-loaded therein, but may be slidably attached to the sheath 12 before deploying the clip 5.

The skin 44 overlies at least a portion of the outer surface 13 of the sheath 12 and the carrier assembly 14. Preferably, the skin 44 extends from the carrier assembly 14 towards the distal end 24 of the sheath 12, e.g., having a proximal end 66 that at least partially covers the clip 5 and a distal end 68 proximate the distal end 24 of the sheath 12. The skin 44 may be substantially secured over the sheath 12, thereby substantially securing the skin 44 from moving axially relative to the sheath 12.

The skin 44 may be separable from the outer surface 13 of the sheath 12 as the carrier assembly 14 is advanced from its proximal position towards the distal end 24 of the sheath 12. For example, the distal end 68 of the skin 44 may terminate adjacent the distal position to which the carrier assembly 14 may be advanced such that the clip 5 may be disposed beyond the distal end 68 of the skin 44 in the distal position.

The skin 44 may be substantially inelastic, e.g., such that the skin 44 may tear when expanded, or alternatively may be elastic. In addition or alternatively, the skin 44 may include an outer surface 70 that is substantially slippery to facilitate advancing the sheath 12 through layers of tissue (not shown), as described further below. The skin 44 may be formed from a variety of materials, e.g., having sufficient flexibility to allow the carrier assembly 14 to be advanced between the skin 44 and the outer surface 13 of the sheath 12 and/or sufficient rigidity to allow the skin 44 to separate or peel away from the outer surface 13 in a predictable and desired manner. Exemplary materials from which the skin 44 may be formed include polytetrafluoroethylene (PTFE), polyethylene terephthalate (PET), polyester, latex, silicone, polyamides, polyurethanes, and/or blends and copolymers thereof. The skin 44 may have a thickness, for example, between about 0.002–0.005 inch. Optionally, the skin 44 may include fibers (not shown) embedded therein or on a surface thereof that may reinforce the skin 44 in a desired manner.

The skin 44 may be bonded to the outer surface 13 of the sheath 12, e.g., using an adhesive, such as an epoxy or urethane. Preferably, the adhesive has sufficient adhesive strength such that the skin 44 may not slide along the outer surface 13 of the sheath 12, yet may be peeled away from the outer surface 13, e.g., as the carrier assembly 14 is advanced towards the distal end 24 of the sheath 12. Alternatively, the skin 44 may be thermally bonded to the outer surface 13, e.g., by heating the skin 44 and/or sheath 12 to at least partially melt or fuse the skin 44 to the outer surface 13.

Alternatively, the skin 44 may be a tube that is securely received around the outer surface 13. For example, the skin 44 may be a length of shrink tube, having an initial diameter that is substantially larger than the sheath 12. The shrink tube may be disposed around the sheath 12, heated, and, consequently, shrunk to wrap around or otherwise engage the outer surface 13 of the sheath 12, either with or without adhesive provided between the skin 44 and the outer surface 13.

Optionally, the skin 44 may include a weakened region 72 extending between the proximal and distal ends 66, 68 of the skin 44, as shown in FIG. 1. The weakened region 72 may be configured to tear or split preferentially as the carrier assembly 14 is advanced towards the distal end 24 of the sheath 12. For example, the weakened region 72 may include a plurality of perforations spaced apart along the skin 44, thereby defining a seam extending between the proximal and distal ends 66, 68 of the skin 44. Alternatively, the weakened region 72 may include a relatively thin-walled seam or region (not shown) of the skin 44 in addition to or instead of the perforated seam.

In a further alternative, fibers (not shown) embedded in the skin 44 may bias the skin 44 to tear preferentially in a desired manner. For example, one or more fibers (not shown) may be may be bonded to the skin 44 that extend between the proximal and distal ends 66, 68 of the skin 44, thereby defining a seam adjacent or between the fibers that may tear preferentially. Alternatively, a plastic or other soft material may be bonded over a braided core (not shown) instead of or in addition to individual fibers, e.g., to create regions of the skin 44 that are resistant to tearing.

Although the weakened region 72 is shown extending substantially parallel to the longitudinal axis 28, the weakened region 72 may extend helically (not shown) or otherwise between the proximal and distal ends 66, 68. The term "axially" as used herein is intended to include any arrangement that may extend generally towards the proximal and/or distal ends 22, 24 of the sheath 12. When the carrier assembly 14 is advanced under the skin 44, the weakened region 72 may tear such that the skin 44 separates or peels away from the outer surface 13, as described further below.

Turning to FIG. 3A, in an alternative embodiment, the skin 44 may be a tubular sleeve 44' that has a relaxed diameter or other periphery that is substantially larger than a diameter or other periphery of the sheath 12. The sleeve 44' may be wrapped around the outer surface 13 of the sheath 12 until a portion of the sleeve 44' is folded over itself to define a flap 45.' The flap 45' may then be laid over an adjacent region 47' of the sleeve 44', whereupon the flap 45' may be bonded or otherwise fastened in order to secure the sleeve 44' to the sheath 12. Thus, as the carrier assembly 14 (not shown in FIG. 3A) is advanced along the sheath 12, the adhesive may fail, and the flap 45' may separate from the adjacent region 47' of the sleeve 44' as the carrier assembly 14 is advanced towards the distal end 24 of the sheath 12.

Turning to FIG. 3B, in another alternative embodiment, the skin 44 may be a tubular sleeve 44" that is slitted generally axially such that the sleeve 44" defines first and second portions 45", 47" including edges. When the edges of the first and second portions 45", 47" abut one another, the sleeve 44" defines a diameter or other periphery that is substantially larger than a diameter or other periphery of the sheath 12. The sleeve 44" may be wrapped around the outer surface 13 of the sheath 12 until the first portion 45" overlies the second portion 47." The first or outer portion 45" may then be bonded or otherwise fastened to the second or inner portion 47" in order to secure the sleeve 44" to the sheath 12. Thus, as the carrier assembly 14 (not shown in FIG. 3B) is advanced along the sheath 12, the adhesive may fail, and the outer portion 45" may separate from the adjacent region 47" as the carrier assembly 14 is advanced towards the distal end 24 of the sheath 12.

The sleeve 44" may have a substantially uniform thickness about its circumference. Alternatively, the sleeve 44" may have a variable thickness about the circumference. For example, the sleeve 44" may have a relatively thin thickness in the first and second portions 45," 47," which may provide a more uniform overall cross-section for the skin 44, as shown in FIG. 3B.

Returning to FIG. 1, the actuator assembly 16 generally includes a handle body 74 and a plurality of telescoping actuator members 76, 78. The handle body 74 includes one or more connectors 80 for connecting the actuator assembly 16 to the sheath 12. For example, the handle body 74 may include a plurality of tabs 80 for engaging mating pockets 34 in the hub 30 or one or more pockets (not shown) for receiving respective tabs (not shown) on the hub 30 of the sheath 12. Thus, the actuator assembly 16 may be substantially permanently attached or removably attached to the sheath 12 by cooperating connectors 34, 80.

In the preferred embodiment shown, the telescoping actuator members 76, 78 include an inner tubular member 76 and an outer tubular member 78. The tubular members 76, 78 may be substantially rigid members having longitudinal slots therein (not shown), thereby defining generally "C" shaped cross-sections over at least a substantial portion of their lengths. Preferably, the longitudinal slots have a width greater than a width of the spoke(s) 31 securing the hub 30 to the sheath 12, thereby allowing the tubular members 76, 78 to slide distally beyond the hub 30, as described further below. The longitudinal slots may extend predetermined distances from ends of the respective tubular members 76, 78, e.g., to limit movement of the tubular members 76, 78 in a desired manner, or may extend the entire length of one or both tubular members 76, 78. Alternatively, the longitudinal slots may be eliminated from the actuator members, such that the actuator members are enclosed wall tubes, if the spokes are eliminated from the hub 30 (not shown).

The distal ends 82, 84 of the tubular members 76, 78 may include detents (not shown) for engaging respective detents on the carrier assembly 14. For example, the detents may be pockets for receiving respective tabs (also not shown) on the carrier and pusher members 40, 42. Thus, movement of the carrier and/or pusher members 40, 42 may be coupled to the inner and outer tubular members 76, 78, respectively. Alternatively, the distal ends 82, 84 of the tubular members 76, 78 may simply abut the carrier and pusher members 40, 42 for pushing the carrier and pusher members 40, 42, thereby coupling distal movement of the carrier and pusher members 40, 42 to the tubular members 76, 78.

In an alternative embodiment, the tubular members 76, 78 may be replaced with one or more elongate rods, bands, or other actuator elements (not shown) that may extend from the handle body 74 and may engage, abut, or otherwise be coupled to the carrier assembly 14. Preferably, the actuator elements are substantially rigid such that they do not buckle when directed distally against the carrier assembly 14. In addition, the actuator elements may be substantially flat such that they slide along the outer surface 13 of the sheath 12, thereby facilitating insertion between the hub 30 and the sheath 12 and/or minimizing a cross-sectional profile.

The actuator assembly 16 also includes a control member, such as a shaft 86, that is coupled to the inner and/or outer tubular members 76, 78. Preferably, the shaft 86 is connected only to the outer tubular member 78, while the inner tubular member 76 is releasably coupled to the outer tubular member 78, as explained further below. Thus, axial movement of one or both of the tubular members 76, 78 may be attained by applying an axial force to the shaft 86.

Optionally, the actuator assembly 16 may also include other components. For example, a lateral port 88 may include an inner passage 89 that communicates with an interior region or lumen (not shown) of the telescoped tubular members 76, 78. Preferably, the lateral port 88 extends through the slots in the tubular members 76, 78, although alternatively, separate slots (not shown) may be provided for the lateral port 88. The lateral port 88 may include one or more detents (not shown) for securing the obturator 18 or other device within the lateral port 88, as described below. In addition, the actuator assembly 16 may include a trigger (not shown) for releasing the obturator 18, as described further below.

Turning to FIGS. 4, 5A, and 5B, the obturator 18 includes a flexible or semi-rigid tubular body or other elongate rail 172 having proximal and distal ends 174, 176. An actuator rod, wire, or other elongate member 178 is slidably disposed with respect to the rail 172, e.g., within a lumen of the rail 172. Preferably, the obturator 18 includes an obturator housing 180 on the proximal end 174. The obturator housing 180 and/or the proximal end 174 of the rail 172 may include one or more detents (not shown) for engaging complementary-shaped detents (also not shown) on the lateral port 88 of the actuator assembly 16. Thus, the obturator 18 may be substantially secured axially with respect to the lateral port 88.

With particular reference to FIGS. 5A and 5B, a distal portion 182 of the obturator 18 may include a substantially rounded, soft, and/or flexible distal tip 184, possibly including a pigtail (not shown) that may facilitate atraumatic advancement of the distal portion 182 into a blood vessel or other body lumen (not shown). The obturator 18 preferably has a length relative to the sheath 12 such that the distal portion 182 may extend beyond the distal end 24 of the sheath 12 when the obturator 18 is fully received in the actuator assembly 16 and sheath 12, as shown in FIG. 4.

One or more, and preferably a plurality of, positioning elements 186 are provided on the distal portion 182 that may be selectively expanded between a substantially axial collapsed configuration (shown in FIG. 5A) and a substantially transverse expanded configuration (shown in FIG. 5B). Preferably, the positioning elements 186 are substantially flexible splines configured for expanding substantially transversely with respect to the longitudinal axis 28. In one embodiment, shown in FIGS. 5A and 5B, the obturator 18 includes a pair of splines 186 disposed generally opposite one another about the distal portion 182. Alternatively, the obturator 18 may include four or any other number of splines (not shown) that are substantially equally spaced about the distal portion 182. Additional information on positioning elements that may be used are disclosed in co-pending application Ser. No. 09/732,835, the disclosure of which is expressly incorporated herein by reference.

Optionally, the splines 186 may include radiopaque markers (not shown) or may be at least partially formed from radiopaque material to facilitate observation of the splines 186 using fluoroscopy or other imaging systems. Alternatively, or in addition, the carrier assembly 14 may include one or more radiopaque markers, e.g., at its distal end (not shown) and/or the clip 5 may include radiopaque marker(s) or may be made from radiopaque material. This may facilitate monitoring the location of the clip 5 relative to the splines 186, as described further below.

Turning to FIGS. 6A–6G, the apparatus 10 may be used to provide access into a blood vessel or other body lumen 90. Preferably, the apparatus 10 is used to deliver a closure device, such as the clip 5, to close and/or seal an incision, puncture, or other opening, such as a passage 92 that extends from a patient's skin 94 through intervening tissue 96, and a wall 98 of the vessel 90. Alternatively, the apparatus 10 may be used to deliver other annular shaped devices (not shown) that may be carried by the carrier assembly 14.

As shown in FIG. 6A, the sheath 12, without the actuator assembly 16 attached and without the obturator 18 therein (both not shown), may be inserted or otherwise positioned within the blood vessel 90, i.e., through the passage 92. The sheath 12 is preferably provided with the carrier assembly 14 in its proximal position, e.g., adjacent to or within the hub 30. The skin 44 may facilitate advancing the sheath 12 through the passage 92, e.g., by providing a slippery outer coating on the skin 44, e.g., of PTFE. In particular, the skin 44 may facilitate advancing the sheath 12 through one or more intervening layers of tissue, such as layers of fascia 97, which may otherwise catch on the sheath 12.

The sheath 12 may be advanced over a guide wire or other rail (not shown) previously positioned through the passage 92 into the blood vessel 90 using conventional procedures. Preferably, the blood vessel 90 is a peripheral vessel, such as a femoral or carotid artery, although other body lumens may be accessed using the sheath 12, as will be appreciated by those skilled in the art. The passage 92, and consequently the sheath 12, may be oriented with respect to the vessel 90, thereby facilitating introducing devices through the lumen 20 of the sheath 12 into the vessel 90 with minimal risk of damage to the vessel 90. One or more devices, such as a guide wire, catheter, and the like (not shown), may be inserted through the sheath 12 and advanced to a desired location within the patient's body. For example, the devices may be used to perform a therapeutic or diagnostic procedure, such as angioplasty, atherectomy, stent implantation, and the like, within the patient's vasculature.

Figure 6B:
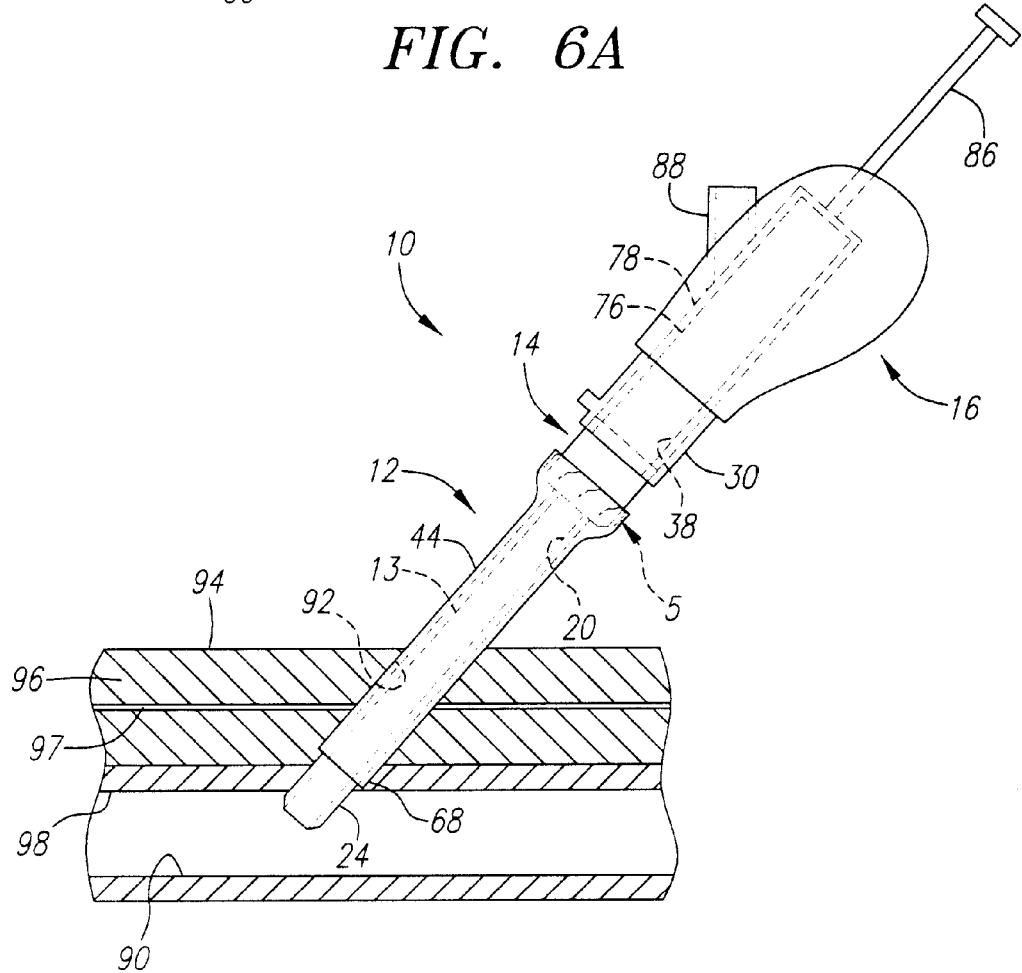

After completing the procedure, any device(s) may be removed from the sheath 12, and the actuator assembly 16 may be attached to the hub 30 of the sheath 12, as shown in FIG. 6B. The tabs 80 on the actuator assembly 16 may be inserted into the pockets 34 on the hub 30 of the sheath 12 (not shown in FIG. 6B), which may align the tubular members 76, 78 such that the distal ends 82, 84 may be inserted freely into the passage 38. If the carrier assembly 14 includes detents (not shown) for being engaged with the distal ends 82, 84 of the tubular member 76, 78, the detents may become engaged as the tabs 80 are inserted into the pockets 34. Alternatively, the tubular members 76, 78 may be advanced into the passage 38 by pushing on the shaft 86 to secure the carrier assembly 14 to the tubular members 76, 78. In a further alternative, the distal ends 82, 84 may simply abut the carrier assembly 14.

Figure 6C:
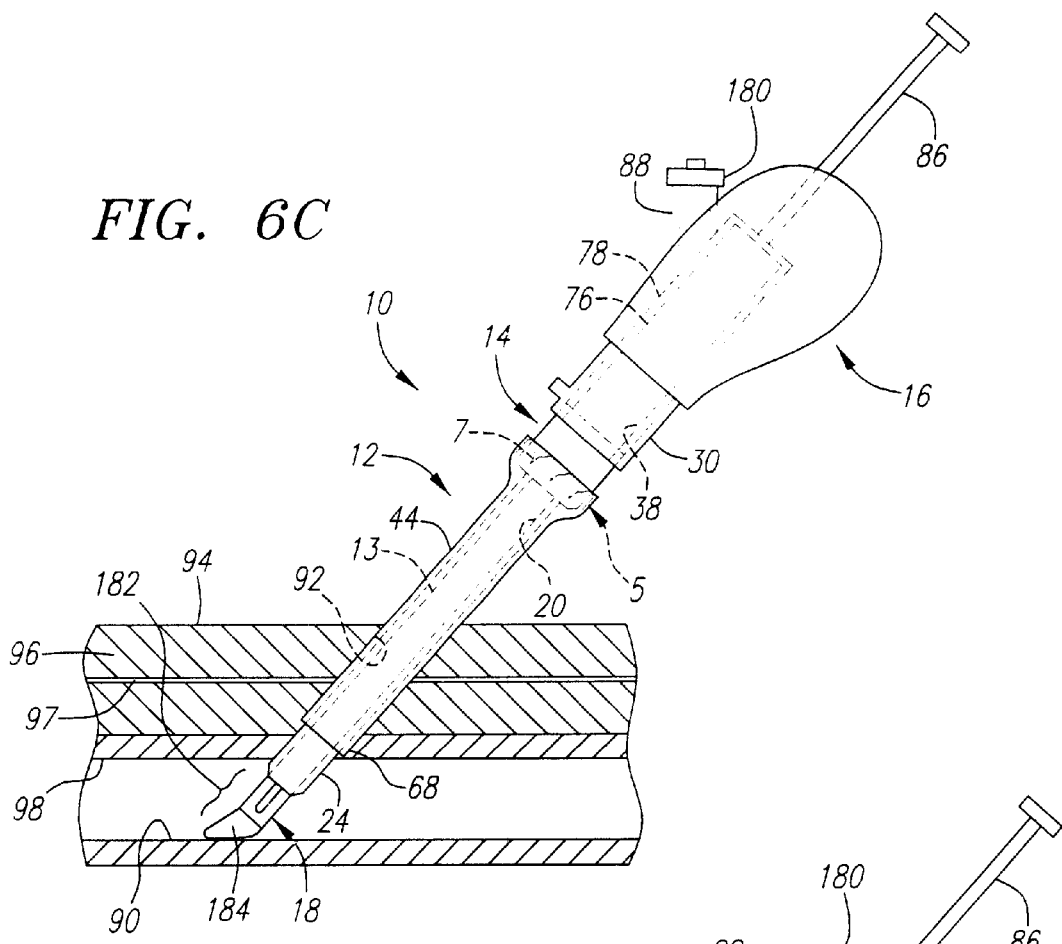

Turning to FIG. 6C, the obturator 18 may then be inserted into the lateral port 88, through the interior of the tubular members 76, 78 and into the lumen 20 of the sheath 12. When the obturator 18 is fully inserted within the sheath 12, the actuator housing 180 may be received in the lateral port 88, and the distal portion 182 of the obturator 18 may extend beyond the distal end 24 of the sheath 12. The distal tip 184 preferably is substantially soft and/or flexible such that the distal portion 182 substantially atraumatically enters the vessel 90. In this fully inserted position, cooperating detents (not shown), e.g., on the actuator housing 180 and the lateral port 88, may be engaged to secure the obturator 18 axially within the actuator assembly 16. Alternatively, the obturator 18 may be pre-attached to the actuator assembly 16, e.g., as a single assembly, as described in co-pending application Ser. No. 10/081,723, filed on the same day as the present application and titled "Apparatus and Methods for Delivering a Closure Element" (attorney docket 262/280). The disclosure of this application and any references cited therein are expressly incorporated herein by reference.

Figure 6D:
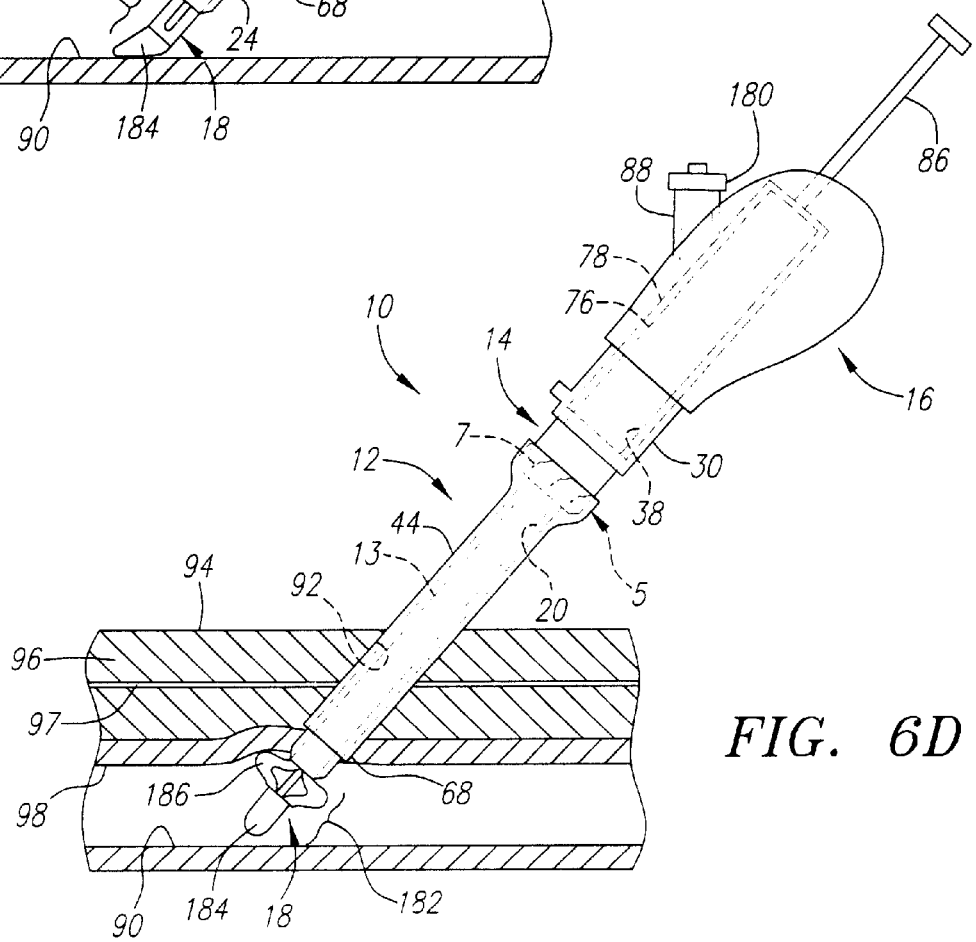

As shown in FIG. 6D, the splines 186 may then be directed to their expanded configuration, for example, by activating a switch (not shown) on the obturator housing 180 of the obturator 18. The sheath 12 and obturator 18 may then be moved in conjunction with one another, e.g., by manipulating the actuator assembly 16. Preferably, the sheath 12 and obturator 18 are together partially withdrawn from the vessel 90, until the splines 186 contact the wall 98 of the vessel 90. Thus, the splines 186 may provide a tactile indication of the position of the sheath 12 with respect to the wall 98 of the vessel 90. In addition, the splines 186 may assist in "presenting" the wall 98 of the vessel 90, e.g., for receiving the clip 5 (or other closure element) if the clip 5 is to engage the wall 98.

Alternatively, one or more bleed back ports (not shown) may be used to position the sheath 12, either instead of or in addition to the obturator 18. Such methods are described in U.S. Pat. No. 6,197,042, issued Mar. 6, 2001 or in co-pending application Ser. No. 09/680,837, filed Oct. 6, 2000. The disclosures of these references and any others cited therein are expressly incorporated herein by reference.

Figure 6E:
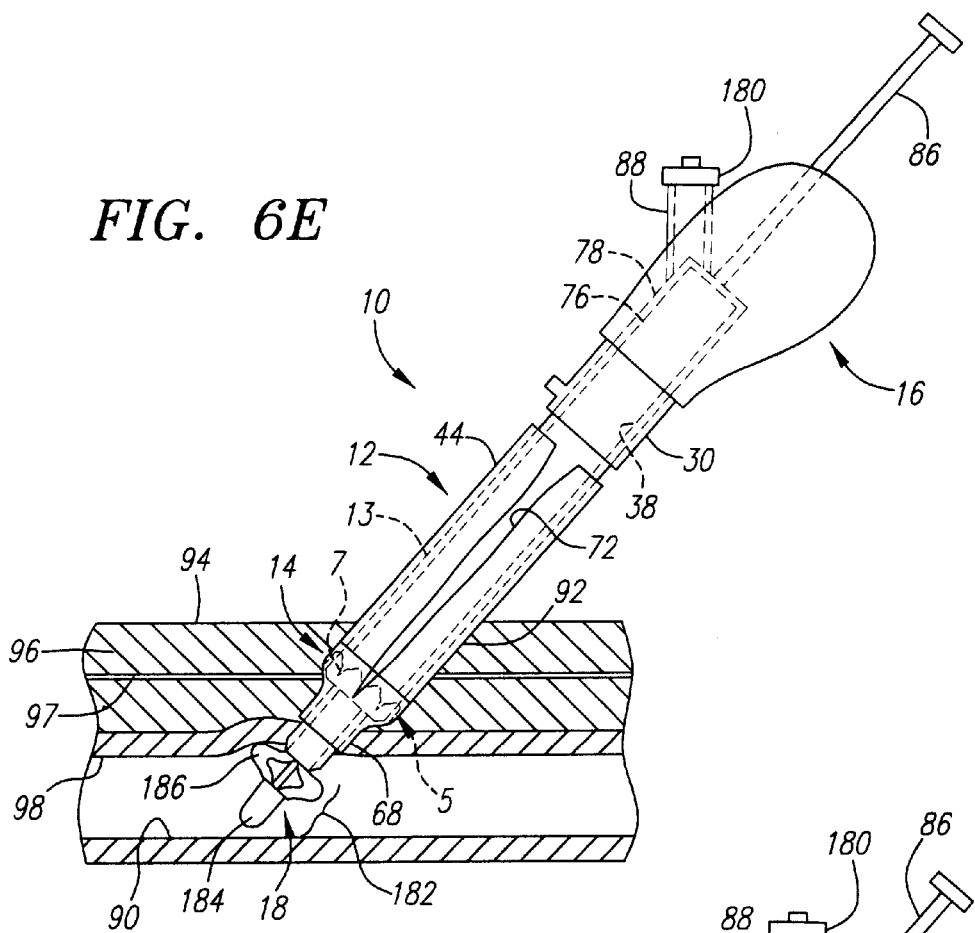

Turning to FIG. 6E, with the sheath 12 properly positioned, the carrier assembly 14 may be advanced along the sheath 12, i.e., into the passage 92 to deliver the clip 5. For example, a distal force may be applied to the shaft 86, thereby advancing the tubular members 76–80 distally over the sheath 12. Because the tubular members 76, 78 are coupled to the carrier assembly 14, the carrier assembly 14 advances along the outer surface 13 of the sheath 12 as the tubular members 76, 78 are pushed distally.

As the carrier assembly 14 is advanced towards the distal end 24 of the sheath 12, the carrier assembly 14 may cause the skin 44 to separate from the outer surface 13 of the sheath 12. Preferably, the distal end 48 of the carrier member 40 includes a ramped region 50 including a ramped distal surface 50*b* (not shown, see FIG. 2). The ramped distal surface 50*b* may slidably engage the skin 44, peeling the skin 44 from the outer surface 13 of the sheath 12 and directing the skin 44 outwardly away from the tines 7 of the clip 5. Thus, the ramped region 50 may ensure that the tines 7 of the clip 5 do not engage the skin 44 and possibly entangle or tear the skin 44 in an undesired manner.

If, as shown in FIG. 1, the skin 44 includes a weakened region 72, the weakened region 72 may tear as the carrier assembly 14 is advanced and the skin 44 is forced to expand due to the increased size of the ramped region 50. Alternatively, if the skin 44 is formed from an elastic material, the skin 44 may simply expand and separate from the outer surface 13 to accommodate the carrier assembly 14 passing under the skin 44. In a further alternative, as shown in FIGS. 3A and 3B, the skin 44 may include a flap 45' or outer portion 45" overlying an adjacent region 47', 47" of the skin 44. The flap 45' or outer portion 45" may be released from the adjacent region 47', 47" as the carrier assembly 14 is advanced towards the distal end of the elongate member, thereby allowing the skin 44 to separate from the outer surface 13. If the skin is bonded to the outer surface 13 of the sheath 12 by an adhesive, the adhesive may allow the skin 44 to be peeled away from the outer surface 13 as the carrier assembly 14 is advanced towards the distal end 24 of the sheath 12.

Because the carrier assembly 14 passes beneath the skin 44, i.e., between the skin 44 and the outer surface 13 of the sheath 12, as it advances along the sheath 12, the skin 44 may facilitate advancing the carrier assembly 14 through one or more intervening layers of fascia 97 or other tissue. Thus, the distal end 48 of the carrier member 40 may not directly contact the layers of fascia 97, thereby minimizing the risk of the carrier assembly 14 and/or the clip 5 catching or otherwise being held up by the intervening layers of fascia 97.

In addition, the tapered configuration of the ramped region 50 may facilitate advancing the carrier assembly through the passage 92 substantially atraumatically. Further, because the clip 5 is substantially covered by the skin 44, the tissue surrounding the passage 92 may not be exposed to the tines 7 on the clip 5, which otherwise may inadvertently catch the tissue and damage the tissue and/or the clip 5.

Figure 6F:
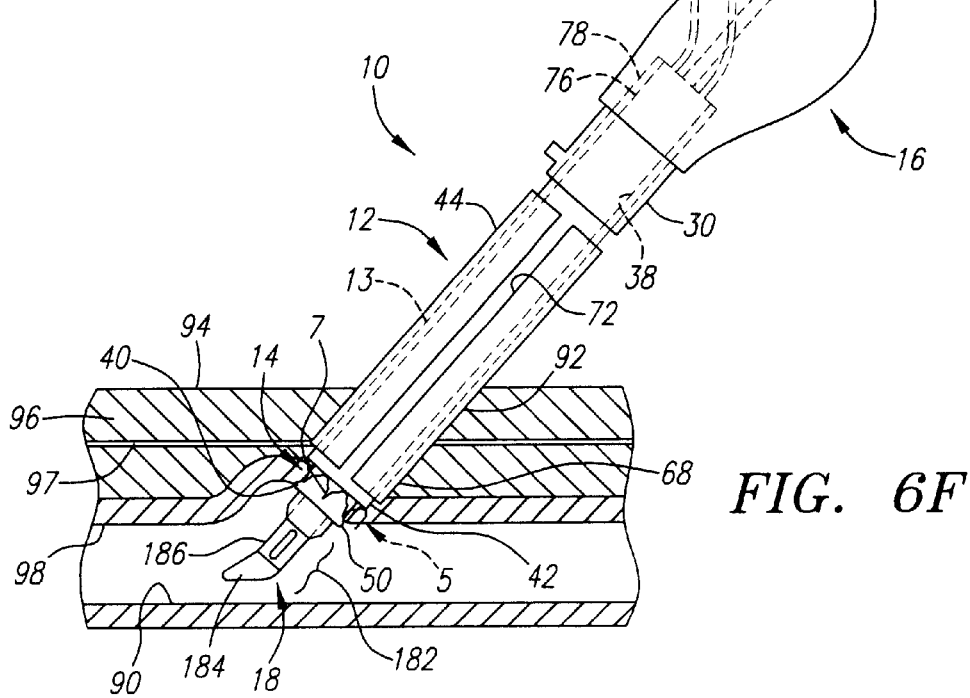

As shown in FIG. 6F, when the carrier assembly 14 reaches a distal position, the clip 5 may become at least partially exposed beyond the distal end 68 of the skin 44. In addition, the inner tubular member 76 may become locked from further distal movement, consequently preventing further distal movement of the carrier member 40 of the carrier assembly 14. Thus, subsequent distal force on the shaft 86 may cause the pusher member 42 to advance distally relative to the carrier member 40, thereby deploying the clip 5 from the carrier member 40. In a preferred embodiment, the ramped region 50 includes a ramped proximal surface 50*a* that may deflect the tines 7 and/or the entire clip 5 radially outwardly. Thus, the ramped region 50 may direct the tines 7 outwardly into surrounding tissue and/or may advance the clip 5 over the ramped region 50 and into tissue beyond the distal end 24 of the sheath 12.

In an alternative embodiment, the skin 44 may cover the clip 5 in the distal position. As the pusher member 42 is advanced distally, the clip 5 may be directed over the ramped region 50, thereby causing the tine 7 to tear through the skin 44 and into surrounding tissue.

To lock the carrier member 40 in the distal position, the inner tubular member 76 may include detents (not shown) that engage with a region of the hub 30 and/or sheath 12 to prevent further distal movement. Alternatively, a tether (also not shown) may be coupled to the carrier member 76 that may prevent further distal movement of the carrier member 76 beyond the distal position.

Returning to FIG. 6F, the splines 186 on the obturator 18 may be collapsed before, during, or after deploying the clip 5 from the carrier assembly 14. Preferably, the splines 186 automatically return to their collapsed configuration before the clip 5 is ejected completely from off of the carrier member 40. For example, a trigger (not shown) in the actuator assembly 16 may release a locking mechanism (also not shown) in the actuator housing 180, whereupon the actuator housing 180 may be biased to collapse the splines 186. In addition, the obturator 18 may include a spring or other biasing mechanism to automatically withdraw the distal portion 182 into the sheath 12 once the splines 186 are collapsed. This feature may avoid any risk of contact between the clip 5 and the splines 186, e.g., which otherwise may risk driving the tines 7 of the clip 5 through the wall 98 of the vessel 90 and into the splines 186. Alternatively, the tines 7 on the clip 5 may be aligned to extend between the splines 186, thereby avoiding any contact between the tines 7 and the splines 186, and the splines 186 may be collapsed after the clip 5 is at least partially deployed.

The relative lengths of the tubular members 76, 78 and the sheath 12 may be selected such that the distal position is at a region proximal to the wall 98 of the vessel 90. For example, it may be desirable to deploy the clip 5 within intervening tissue between the patient's skin and the wall 98 of the vessel 90. Alternatively, the clip 5 may be deployed such that the tines 7 are driven into or through the wall 98 of the vessel 90, as shown in FIGS. 6F and 6G.

Figure 6G:
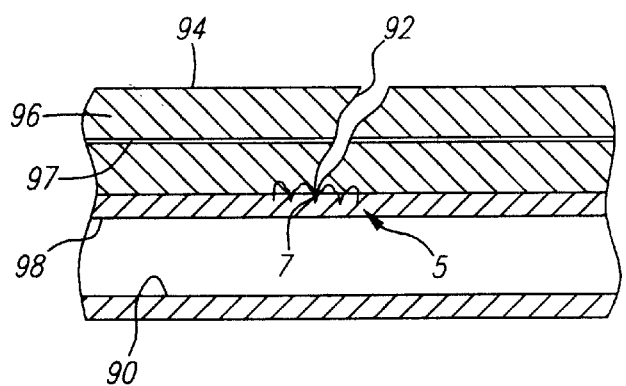

Once the clip 5 is successfully delivered, the apparatus 10 may be withdrawn from the passage 92, leaving the clip 5 to close the opening in the wall 98 or otherwise seal the passage 92, as shown in FIG. 6G. If the splines 64 of the locator member 14 are not automatically collapsed while advancing the housing 24, the splines 64 may be affirmatively collapsed, e.g., by depressing a switch (not shown) on the actuator housing 180, either before or after deployment of the clip 5. The entire apparatus 10 may then be removed in one step, or alternatively, the obturator 18 may first be withdrawn from the sheath 12 before withdrawing the sheath 12, thereby leaving the clip 5 in place to close and/or seal the passage 92. In an alternative embodiment, the distal tip 184 of the obturator 18 may be formed from a bioabsorbable and/or expandable material, e.g., collagen, and may be detachable such that the distal tip 184 may be released within the passage 92 to enhance sealing.

Figure 7:
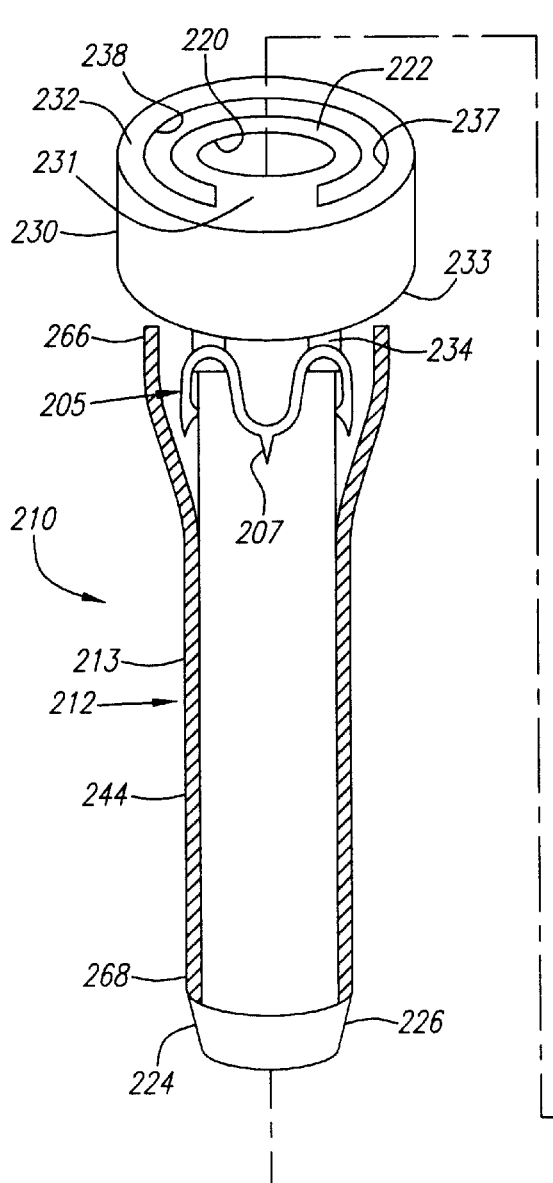
FIG. 7 is a perspective view of a second preferred embodiment of an apparatus for delivering a closure element, including an introducer sheath, and an actuator assembly, in accordance with the present invention.
Figure 7:
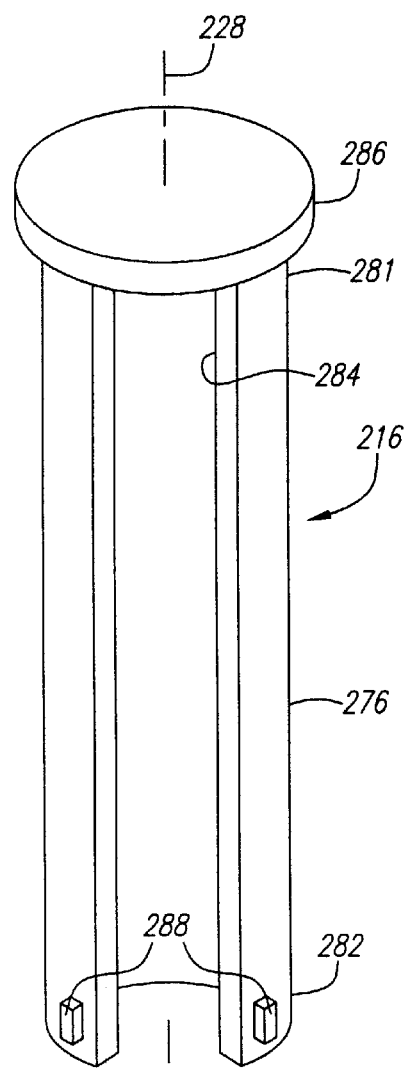

Turning to FIGS. 7–9, another embodiment of an apparatus 210 is shown for delivering a closure element, such as a clip 205, into an opening through tissue (not shown) for closing and/or sealing the opening. Generally, the apparatus 210 includes an introducer sheath 212, a plunger or actuator assembly 216 that may be coupled to the sheath 212 and/or clip 205, and a skin 244 overlying an outer surface 213 of the sheath 212 and/or the clip 205. Optionally, the apparatus 210 may also include a locator member or obturator 218 (not shown, see FIG. 10) that may be insertable through the actuator assembly 216 and/or sheath 212 for assisting positioning of the apparatus, similar to the embodiment described above.

The sheath 212 is generally a substantially flexible or semi-rigid tubular member including a lumen 220 extending along a longitudinal axis 228 between its proximal and distal ends 222, 224. The distal end 224 has a size and shape to facilitate insertion into an opening through tissue (not shown), e.g., having a tapered tip 226 for facilitating substantially atraumatic introduction through a passage and/or at least partially into a blood vessel or other body lumen accessed via the passage. The lumen 220 has a size for accommodating inserting one or more devices therethrough, such as the obturator 218, a catheter, a guidewire, and the like (not shown). The sheath 212 may also include a seal (not shown) that may provide a fluid-tight seal, yet accommodate inserting one or more devices into the lumen 20, similar to the embodiment described above.

An annular hub 230 is provided on the proximal end 222 of the sheath 212, e.g., attached by one or more radial spokes 231. Preferably, the hub 230 and the sheath 212 define an annular or "C" shaped passage 238 between the outer surface 213 of the sheath 212 and an inner surface 237 of the hub 230 that extends substantially parallel to the longitudinal axis 228. The actuator assembly 216 may be slidably coupled to the hub 230, e.g., by inserting the distal end of the actuator assembly 216 into the passage 238. Alternatively, the hub 230 may include one or more connectors (not shown) on its proximal end 232 for cooperating with mating connectors (also not shown) on a housing (also not shown) of the actuator assembly 216, similar to the embodiment described above. Optionally, the hub 230 may include a side port (not shown) that communicates with the lumen 220, for example, to allow infusion of fluids into the lumen 220 through the sheath 212 and/or to provide a "bleed back" indicator, as described above.

The hub 230 includes a plurality of spacers or alignment tabs 234 extending from a distal end 233 of the hub 230. Preferably, the tabs 234 are spaced apart from the outer surface 213 of the sheath 212 and extend substantially parallel to the longitudinal axis 228. For example, as best seen in FIGS. 9A–9C, an inner surface 234a of the tabs 234 may be aligned with the inner surface 237 of the hub 230 such that the tabs 234 do not obstruct the passage 238. In a preferred embodiment, the tabs 234 are spaced evenly about the circumference of the hub 230, e.g., in a desired orientation relative to the passage 238, as explained further below. Alternatively, an annular ridge (not shown) may be provided that extends continuously around the circumference of the hub 230, thereby defining a single, continuous spacer.

The clip 205, best seen in FIG. 8, is an annular-shaped member including proximal and distal ends 206, 208 and a plurality of tissue engaging elements 207 extending from the distal end 208. In a preferred embodiment, the clip 205 includes a plurality of alternating diagonal elements 209 extending between the proximal and distal ends 206, 208. The proximal and distal ends 206, 208 of the clip 205 include curved elements connecting adjacent diagonal elements 209, the curved elements alternating between the proximal and distal ends 206, 208 around the circumference of the clip 205 such that the clip 205 defines a substantially continuous serpentine or zigzag pattern about the circumference. Alternatively, the clip may include one or more loops (not shown) between adjacent tissue engaging elements, which may enhance a flexibility of the clip 205. Additional information on such a clip may be found in co-pending application Ser. No. 10/081,726, filed on the same day as the present application, and titled "Closure Apparatus and Methods for Making and Using Them" (attorney docket no. 260/099). The disclosure of this application and any references cited therein are expressly incorporated herein by reference.

Preferably, the tissue engaging elements are tines 207 extending distally from the distal end 208. Optionally, the tines 207 or the distal end 208 may include offset elements 204, e.g., on an inner surface thereof for maintaining the tines 207 away from the outer surface 213 of the sheath, as best seen in FIGS. 9A–9C. The offset elements 204 may simply be rounded tabs formed on an inner surface of the clip 205, e.g., having a thickness greater than the rest of the clip 205 or may be separate elements attached to the clip 205.

In a preferred embodiment, the tines 207 are biased towards one another, e.g., for engaging tissue surrounding an opening and drawing the tissue inwardly to substantially close and/or seal the opening. For example, the distal curved elements 208 of the clip 205 may be biased to move inwardly and/or the proximal curved elements 206 may be biased to move outwardly. Thus, in a preferred embodiment, the clip 205 is biased towards a planar configuration with the tines 207 directed inwardly towards one another (not shown). Additional information on clips appropriate for use with the apparatus 210 may be found in applications Ser. Nos. 09/546,998 and 09/610,238, incorporated by reference above.

Returning to FIG. 8, the clip 205 is initially carried adjacent the proximal end 222 of the sheath 212 such that the proximal end 206 of the clip 205 overlies or engages the tabs 234 on the hub 230, thereby retaining the proximal end 206 of the clip 205 away from the outer surface 213 of the sheath 212 and in a desired orientation. The spacing of the tabs 234 on the hub 230 may correspond to the spacing of the proximal curved elements 206 of the clip 205, e.g., such that each proximal curved element 206 is held away from the outer surface 213 of the sheath 212 by a respective tab 234. Preferably, the tabs 234 hold the clip 205 in the desired orientation to ensure that the clip 205 is properly coupled to the actuator assembly 216, as described further below. In this initial position, the distal end 208 of the clip 205 may rest against the outer surface 213 of the sheath 212, although the tines 207 may be retained away from the outer surface 213 by the offset elements 204.

The skin 244 may overlie at least a portion of the outer surface 213 of the sheath 212 and the clip 205. Preferably, the skin 44 extends from the clip 205 towards the distal end 24 of the sheath 12, e.g., having a proximal end 266 that at least partially covers the clip 205 and a distal end 268 proximate the distal end 224 of the sheath 212. The skin 244 may be substantially secured over the sheath 212, thereby substantially securing the skin 244 from moving axially relative to the sheath 212, e.g., by friction and/or by an adhesive, similar to the embodiments described above. In a further alternative, the skin 244 may be eliminated from any of the embodiments described herein.

The skin 244 may be separable from the outer surface 213 of the sheath 212 as the clip 205 is advanced from its proximal position towards the distal end 224 of the sheath 212. The skin 244 may be formed from substantially inelastic materials, e.g., such that the skin 244 may tear when expanded, or alternatively from elastic materials, similar to the embodiments described above. Optionally, the skin 244 may include a weakened region (not shown) extending between the proximal and distal ends 266, 268 of the skin 244, and/or may include fibers (not shown) embedded in the skin 244 may bias the skin 244 to tear preferentially in a desired manner, as explained above.

The actuator assembly 216 generally includes a substantially rigid tubular member 276 including proximal and distal ends 281, 282. In a preferred embodiment, the tubular member 276 includes a slot 284 (not shown, see FIG. 7) extending at least partially between the proximal and distal ends 281, 282. The tubular member 276 has a "C" shaped cross-section defining a diameter corresponding generally to the outer surface 213 of the sheath 212 and has a thickness such that the distal end 282 may be slidably inserted into the passage 238 between the hub 230 and the sheath 212, as explained further below. The slot 284 may have a width corresponding to the spoke 231, thereby allowing the tubular member 276 to be directed distally through the passage 238 without substantial interference by the spoke 231. Alternatively, the actuator assembly 216 may include a plurality of substantially rigid bands separated by slots (not shown) that generally define a tubular structure or otherwise conform generally to the shape of the outer surface 213 of the sheath 212.

Optionally, the actuator assembly 216 may include a housing (not shown) that may be connected to the hub 230 and/or directly to the proximal end 220 of the sheath 212. The housing may secure the actuator assembly 216 to the sheath 212, may limit movement of the tubular member 276, and/or may contain internal components (not shown) of the actuator assembly 216, similar to the embodiment described above. In addition, a housing may ensure that the actuator assembly 216 is coupled to the sheath 212 in a desired orientation, e.g., to align the slot 284 of the tubular member 276 with the spoke 231 securing the hub 230 to the sheath 212, as explained further below.

The tubular member 276 includes a plurality of protrusions 288 on the distal end 282 for coupling distal movement of the clip 205 to the tubular member 276. Preferably, the protrusions 288 are tabs that extend radially outwardly from the distal end 282 of the tubular member 276. The protrusions 288 may be spaced apart about the circumference of the tubular member 276, preferably in a predetermined relationship to the tabs 234 extending from the hub 230 of the sheath 212. Preferably, the protrusions 288 are disposed between adjacent tabs 234 such that a protrusion 288 may be aligned with each distal curved element 208 of the clip 205 when the proximal curved elements 206 are engaged over the tabs 234. Thus, the distal curved elements 208 of the clip 205 may provide for pockets for receiving the protrusions 288 to couple the clip 205 to the tubular member 276.

During assembly of the apparatus 210, the distal end 282 of the tubular member 276 may be aligned with the passage 238 of the sheath 212, as shown in FIG. 7. The distal end 282 may be inserted into the passage 238, as shown in FIG. 9A, until the protrusions 288 pass between the tabs 234, and, consequently, between the proximal curved elements 206 of the clip 205. Thus, as the tubular member 276 is advanced distally, the protrusions 288 enter the pockets defined by the distal curved elements 208 and engage the distal curved elements 208 of the clip 205, as shown in FIG. 9B. With the clip 205 coupled to the tubular member 276, further distal movement of the tubular member 276 causes the clip 205 to move distally, as shown in FIG. 9C. As this occurs, the proximal curved elements leave the tabs 234 and travel along the outer surface 213 of the sheath 212.

If the apparatus 210 includes a skin 244 overlying the outer surface 213 of the sheath 212, the skin 244 may be separated from the outer surface 213 as the clip 205 is advanced towards the distal end 224 of the sheath 212, similar to the embodiment described above. In one embodiment, the protrusions 288 may have a height that is greater than a thickness of the clip 205 such that the protrusions 288 extend radially outwardly from the outer surface 213 of the sheath 212 a greater distance than the clip 205. Thus, the protrusions 288 may cause the skin 244 to separate from the outer surface 213, thereby minimizing the risk of the tines 207 of the clip 205 catching on the skin 244. Alternatively, the tines 206 may be oriented to prevent them from catching on the skin 244 or the skin 244 may include an interior surface that is substantially slippery such that the tines 207 may slide along the skin 244.

The apparatus 210 may be used to deliver the clip 205 or other closure element, similar to the embodiment described above. Initially, the sheath 212, without the actuator assembly 216, may be inserted or otherwise positioned within a blood vessel through a puncture or other passage. The sheath 212 is provided with the clip 205 in its proximal position, e.g., with the proximal end 206 held by the tabs 234 extending from the hub 230. The sheath 212 may be advanced over a guide wire or other rail (not shown) previously positioned through the passage into the blood vessel using conventional procedures. In a preferred method, the blood vessel is a peripheral vessel, such as a femoral or carotid artery, although other body lumens may be accessed using the sheath 212, as will be appreciated by those skilled in the art.

One or more devices, such as a guide wire, catheter, and the like (not shown), may be inserted through the sheath 212 and advanced to a desired location within the patient's body. For example, the devices may be used to perform a therapeutic or diagnostic procedure, such as angioplasty, atherectomy, stent implantation, and the like, within the patient's vasculature. After completing the procedure, any device(s) may be removed from the sheath 212, and the actuator assembly 216 may be inserted into the passage 238, as shown in FIGS. 9A and 9B, and as described above. If the actuator assembly 216 includes a housing (not shown), the housing may be attached to the hub 230 and/or to the sheath 212.

Alternatively, the clip 205 may be pre-loaded on the actuator assembly 216, rather than on the sheath 212. For example, the clip 205 may be disposed on the distal end 282 such that the protrusions 288 are disposed between the diagonal elements 209 and/or the distal curved elements 208. In this alternative, the spacers 234 on the hub 230 may be eliminated. Thus, the clip 205 may be advanced through the passage 238 as the actuator assembly 216 is coupled to the sheath 212. In a further alternative, a pusher member (not shown) may be disposed around the actuator assembly 216 for deploying the clip 205 from the actuator assembly 216.

Figure 10:
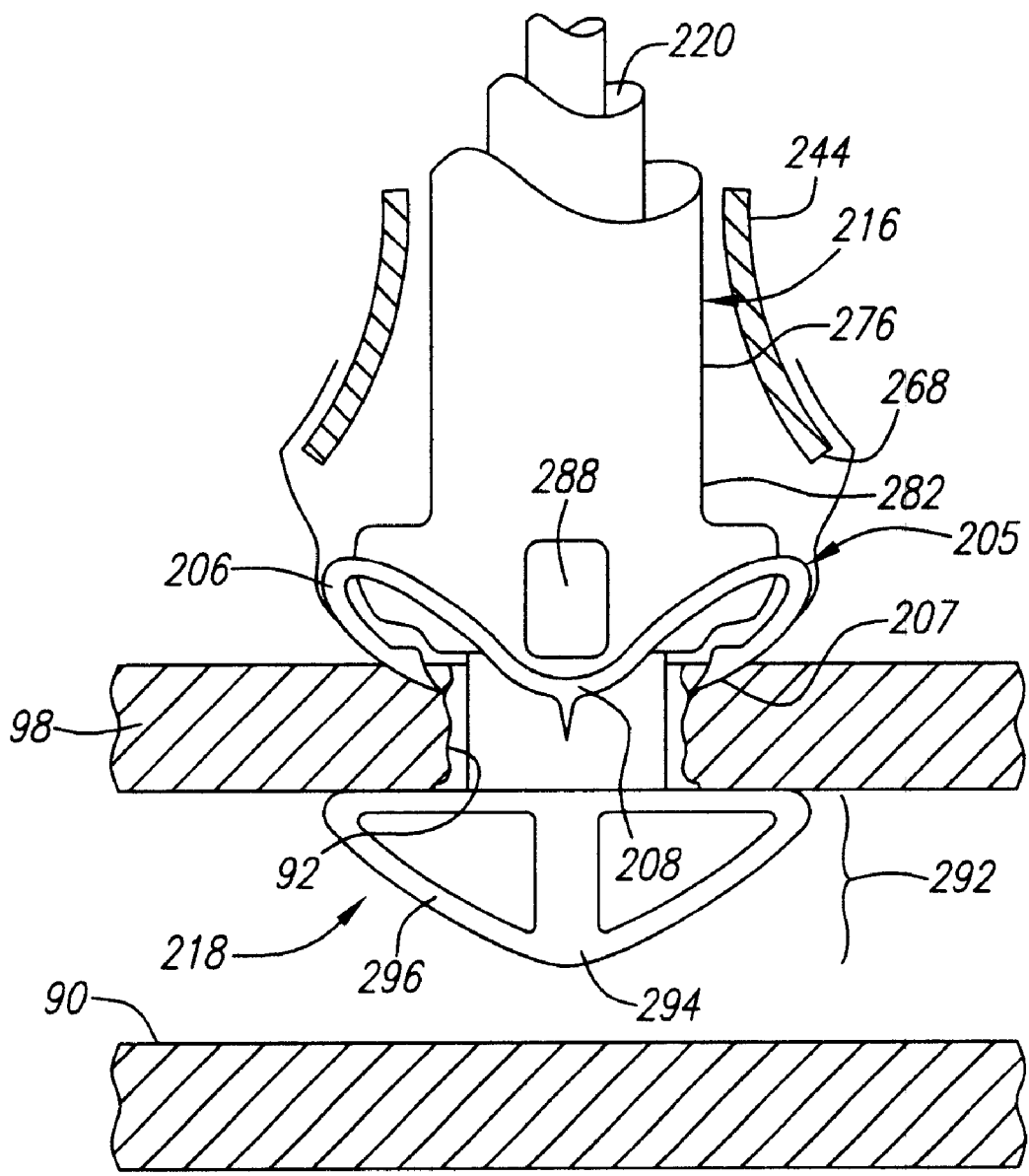
FIG. 10 is a cross-sectional view of a blood vessel, showing a closure element being delivered by the apparatus of FIG. 7.

As shown in FIG. 10, an obturator 218, similar to the obturator 18 described above, may then be inserted into the lumen 220 of the sheath 212, e.g., through a lateral port (not shown) communicating with the actuator assembly 216 or the hub 230. The distal tip 294 preferably is substantially soft and/or flexible such that the distal portion 292 substantially atraumatically enters the vessel. The obturator 218 may include a plurality of splines 296 on the distal portion 292 that are expandable from an axial collapsed configuration to a transverse expanded configuration, such as that shown in FIG. 10. In a preferred embodiment, the splines 296 are formed from substantially rigid segments, e.g., from stainless steel, connected by hinged regions such that the splines 296 may bend to the expanded configuration. When the obturator 218 is fully inserted into the sheath 212, the distal portion 292 extends beyond the distal end 224 of the sheath 212. Cooperating detents (not shown), e.g., on the obturator 218 and the lateral port, may be engaged to secure the obturator 218 with respect to the sheath 212.

With the obturator 218 inserted into the sheath 212, the splines 296 may be directed to their expanded configuration, for example, by activating a switch (not shown) on the proximal end of the obturator 218. The sheath 212 and obturator 218 may then be moved in conjunction with one another and preferably are together partially withdrawn from the vessel 90, until the splines 296 contact the wall 98 of the vessel 90. Thus, the splines 296 may provide a tactile indication of the position of the sheath 12 with respect to the wall 98 of the vessel 90. In addition, the splines 296 may assist in "presenting" the wall 98 of the vessel 90, e.g., for receiving the clip 205 (or other closure element) if the clip 205 is to engage the wall 98. Alternatively, one or more bleed back ports (not shown) may be used to position the sheath 212, either instead of or in addition to the obturator 18.

With the sheath 212 properly positioned, the clip 205 may be advanced along the sheath 212, i.e., into the passage 92, as described above. A distal force may be applied to the tubular member 276, thereby advancing the clip 205 distally over the sheath 212. As the clip 205 is advanced towards the distal end 224 of the sheath 212, the protrusions 288 and/or the clip 205 may cause the skin 244 to separate from the outer surface 213 of the sheath 212. Because the clip 205 passes beneath the skin 244, i.e., between the skin 244 and the outer surface 213, as it advances along the sheath 212, the skin 244 may facilitate advancing the clip 205 through one or more intervening layers, e.g., of fascia (not shown), similar to the embodiment described above.

As shown in FIG. 10, when the clip 205 reaches the distal end 224 of the sheath 212, the clip 205 may become at least partially exposed beyond the distal end 268 of the skin 244. Preferably, the clip 205 is entirely exposed beyond the distal end 268 of the skin 244 and the tines 207 are driven into or otherwise engage tissue adjacent the distal end 224 of the sheath 212. When the clip 205 is exposed, the clip 205 may begin to move towards a planar configuration, as shown in FIG. 10, such the proximal curved elements 206 move away from the distal end 282 of the tubular member 276. The splines 296 on the obturator 218 may be collapsed before, during, or after deploying the clip 205, and the apparatus 210 may be withdrawn from the passage 92. The clip 205 may then return to a substantially planar configuration, thereby closing and/or sealing the passage 92, similar to the embodiment shown in FIG. 6G.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for delivering a closure device, comprising:
   an elongate member comprising proximal and distal ends defining a longitudinal axis therebetween, and an outer surface extending between the proximal and distal ends;
   a hub on the proximal end of the elongate member, the hub comprising one or more spacers spaced away from the outer surface of the elongate member;
   a closure element comprising a generally annular-shaped body comprising proximal and distal ends and a plurality of tissue engaging portions extending from the distal end, the proximal end being held away from the outer surface of the elongate member by the one or more spacers; and
   an actuator assembly comprising an elongate actuator member slidable between the one or more spacers and the outer surface of the elongate member, the actuator member comprising one or more protrusions for engaging the closure element, whereby distal movement of the actuator member advances the closure element towards the distal end of the elongate member.

2. The apparatus of claim 1, wherein the hub comprises an annular hub defining a passage between the annular hub and the outer surface of the elongate member.

3. The apparatus of claim 2, wherein the annular hub is attached to the elongate member by one or more radial spokes.

4. The apparatus of claim 3, wherein the actuator member comprises a tubular member defining a "C" shaped cross-section for inserting the tubular member through the passage around the one or more radial spokes.

5. The apparatus of claim 1, wherein the actuator member comprises a tubular member comprising a distal end, and wherein the one or more protrusions comprises a plurality of tabs extending radially outwardly from the distal end of the tubular member.

6. The apparatus of claim 5, wherein the closure element comprises a plurality of pockets for receiving respective tabs on the tubular member therein.

7. The apparatus of claim 6, wherein the closure element comprises a plurality of alternating diagonal elements extending between the proximal and distal ends of the closure element, and wherein the distal end of the closure element comprises curved elements connecting adjacent diagonal elements, the curved elements defining the pockets.

8. The apparatus of claim 6, wherein the tissue engaging elements comprise tines extending distally from the distal end of the closure element, and wherein the closure element comprises offset elements on an inner surface of the curved elements on the distal end of the closure element for maintaining the tines away from the outer surface of the elongate member.

9. The apparatus of claim 1, wherein the actuator assembly is attachable to the hub.

10. The apparatus of claim 1, wherein the elongate member comprises a sheath comprising a lumen extending between proximal and distal ends thereof.

11. The apparatus of claim 1, further comprising a skin overlying at least a portion of the outer surface of the elongate member between the carrier assembly and the distal end of the elongate member, and at least partially overlying the closure element, the skin being separable from the outer surface as the closure element is advanced towards the distal end of the elongate member.

12. The apparatus of claim 11, wherein the skin comprises a weakened region extending axially along the skin, the weakened region configured to tear as the carrier assembly is advanced from the proximal end towards the distal end of the elongate member.

13. The apparatus of claim 12, wherein the weakened region comprises at least one of a thin region and a perforated region of the skin.

14. The apparatus of claim 11, wherein the skin comprises a flap extending axially along the outer surface of the elongate member and overlying an adjacent region of the skin, the flap being bonded to the adjacent region such that the flap may be separated from the adjacent region as the carrier assembly is advanced towards the distal end of the elongate member.

15. The apparatus of claim 14, wherein the skin comprises a tubular member extending around the outer surface of the elongate member, and wherein the flap comprises a region of the tubular member that is folded over itself to secure the tubular member to the outer surface of the elongate member.

16. The apparatus of claim 15, wherein the tubular member comprises a periphery that is larger than a periphery of the elongate member when the skin is separated from the outer surface.

17. The apparatus of claim 11, wherein the closure element passes between the skin and the outer surface as it is advanced towards the distal end of the elongate member.

18. The apparatus of claim 17, wherein the protrusions have a height that is greater than a thickness of the closure element such that the protrusions extend radially outwardly from the outer surface of the elongate member a greater distance than the closure element.

19. The apparatus of claim 11, wherein the skin is bonded to the outer surface of the elongate member by an adhesive, the adhesive having sufficient adhesive strength such that the skin may be peeled away from the outer surface as the carrier assembly is advanced towards the distal end of the elongate member.

20. The apparatus of claim 1, wherein the closure element is carried on a distal end of the actuator member when the closure element is engaged by the one or more protrusions, and wherein the actuator assembly comprises an outer member slidable on the actuator member for deploying the closure element from the distal end of the actuator member.

21. The apparatus of claim 1, wherein said closure element is provided with one or more offset elements which space the tissue engaging portions of the closure element form the outer surface of the elongate member.

22. An apparatus for delivering a closure device, comprising:
an elongate member comprising proximal and distal ends defining a longitudinal axis therebetween, and an outer surface extending between the proximal and distal ends;
one or more spacers on the proximal region of the elongate member;
a closure element comprising a generally annular-shaped body comprising proximal and distal ends and a plurality of tissue engaging portions extending from the distal end, the proximal end being held away from the outer surface of the elongate member by the one or more spacers; and
an actuator assembly comprising an elongate actuator member slidable between the one or more spacers and the outer surface of the elongate member, the actuator member being aligned with the elongate member and having one or more protrusions for engaging the closure element, whereby distal movement of the actuator member advances the closure element towards the distal end of the elongate member.

23. The apparatus of claim 22, wherein the actuator member comprises a tubular member comprising a distal region, and wherein the one or more protrusions comprises a plurality of tabs extending radially outwardly from the distal region of the tubular member.

24. The apparatus of claim 23, wherein the closure element comprises a plurality of pockets for receiving respective tabs on the tubular member therein.

25. The apparatus of claim 24, wherein the closure element comprises a plurality of alternating diagonal elements extending between the proximal and distal ends of the closure element, and wherein the distal end of the closure element comprises curved elements connecting adjacent diagonal elements, the curved elements defining the pockets.

26. The apparatus of claim 24, wherein the tissue engaging elements comprise tines extending distally from the distal end of the closure element, and wherein the closure element comprises offset elements on an inner surface of the curved elements on the distal end of the closure element for maintaining the tines away from the outer surface of the elongate member.

27. The apparatus of claim 22, wherein the elongate member comprises a sheath having a lumen extending between the proximal and distal ends thereof.

28. The apparatus of claim 22, further comprising a skin overlying at least a portion of the outer surface of the elongate member between the carrier assembly and the distal end of the elongate member, and at least partially overlying the closure element, the skin being separable from the outer surface as the closure element is advanced towards the distal end of the elongate member.

29. The apparatus of claim 28, wherein the skin comprises a weakened region extending axially along the skin, the weakened region configured to tear as the carrier assembly is advanced from the proximal end towards the distal end of the elongate member.

30. The apparatus of claim 29, wherein the weakened region comprises at least one of a thin region and a perforated region of the skin.

31. The apparatus of claim 28, wherein the skin comprises a flap extending axially along the outer surface of the elongate member and overlying an adjacent region of the skin, the flap being bonded to the adjacent region such that the flap may be separated from the adjacent region as the carrier assembly is advanced towards the distal end of the elongate member.

32. The apparatus of claim 31, wherein the skin comprises a tubular member extending around the outer surface of the elongate member, and wherein the flap comprises a region of the tubular member that is folded over itself to secure the tubular member to the outer surface of the elongate ember.

33. The apparatus of claim 32, wherein the tubular member comprises a periphery that is larger than a periphery of the elongate member when the skin is separated from the outer surface.

34. The apparatus of claim 28, wherein the closure element passes between the skin and the outer surface as it is advanced towards the distal end of the elongate member.

35. The apparatus of claim 34, wherein the protrusions have a height that is greater than a thickness of the closure element such that the protrusions extend radially outwardly from the outer surface of the elongate member a greater distance than the closure element.

36. The apparatus of claim 28, wherein the skin is bonded to the outer surface of the elongate member by an adhesive, the adhesive having sufficient adhesive strength such that the skin may be peeled away from the outer surface as the carrier assembly is advanced towards the distal end of the elongate member.

37. The apparatus of claim 22, wherein the closure element is carried on a distal region of the actuator member when the closure element is engaged by the one or more protrusions, and wherein the actuator assembly comprises an outer member slidable on the actuator member for deploying the closure element from the distal end of the actuator member.

38. The apparatus of claim 22, wherein said closure element is provided with one or more offset elements which space the tissue engaging portions of the closure element from the outer surface of the elongate member.

* * * * *